US009753043B2

(12) United States Patent
Lebowitz et al.

(10) Patent No.: US 9,753,043 B2
(45) Date of Patent: Sep. 5, 2017

(54) METHODS AND ALGORITHMS FOR AIDING IN THE DETECTION OF CANCER

(71) Applicant: 20/20 GENESYSTEMS, INC., Rockville, MD (US)

(72) Inventors: Michael Lebowitz, Baltimore, MD (US); Ronald Shore, Rockville, MD (US)

(73) Assignee: 20/20 GeneSystems, Inc., Rockville, MD (US)

( * ) Notice: Subject to any disclaimer, the term of this patent is extended or adjusted under 35 U.S.C. 154(b) by 0 days.

(21) Appl. No.: 13/718,457

(22) Filed: Dec. 18, 2012

(65) Prior Publication Data
US 2013/0196868 A1 Aug. 1, 2013

Related U.S. Application Data

(60) Provisional application No. 61/577,083, filed on Dec. 18, 2011.

(51) Int. Cl.
*G01N 33/68* (2006.01)
*G01N 33/574* (2006.01)

(52) U.S. Cl.
CPC ... *G01N 33/6893* (2013.01); *G01N 33/57484* (2013.01); *G01N 2800/50* (2013.01); *G01N 2800/60* (2013.01)

(58) Field of Classification Search
CPC .............. G01N 33/6893; G01N 33/57484
USPC ............................................................ 506/9
See application file for complete search history.

(56) References Cited

U.S. PATENT DOCUMENTS

| 2003/0174873 | A1* | 9/2003 | Giger et al. ............ 382/128 |
| 2007/0178504 | A1 | 8/2007 | Colpitts et al. |
| 2008/0133141 | A1* | 6/2008 | Frost ........................ 702/19 |
| 2008/0160546 | A1 | 7/2008 | Colpitts et al. |
| 2009/0176228 | A1* | 7/2009 | Birse ................ C12Q 1/6886 435/6.11 |
| 2009/0298097 | A1* | 12/2009 | Harris et al. ............. 435/7.23 |
| 2011/0053158 | A1 | 3/2011 | Mambo et al. |
| 2012/0071334 | A1* | 3/2012 | Colpitts et al. ............ 506/9 |
| 2012/0108462 | A1 | 5/2012 | Keller et al. |

FOREIGN PATENT DOCUMENTS

WO 2009006323 1/2009

OTHER PUBLICATIONS

Kooter et al., Circulation, Aug. 9, 2011, pp. 741-745.*
Mantel et al., Journal of the National Cancer Institute, 1959, vol. 22, No. 2, pp. 719-729.*
Bach et al., Journal of the National Cancer Institute, Mar. 19, 2003, 95(6), pp. 470-478.*
Clark et al., Drug and Alcohol Dependence 77, 2005, pp. 13-21.*
American Cancer Society. Cancer Facts & Figures 2011. Atlanta: American Cancer Society; 2011.
Bach, Peter B., et al. "Screening for Lung Cancer* ACCP Evidence-Based Clinical Practice Guidelines (2nd Edition)." CHEST Journal. Sep. 2007. vol. 132, No. 3 Supplement. pp. 69S-77S.
Bianchi, Fabrizio, et al. "A serum circulating miRNA diagnostic test to identify asymptomatic high-risk individuals with early stage lung cancer." EMBO Molecular Medicine. 2011. vol. 3, No. 8. pp. 495-503.
Bigbee, W.L.P., et al. "A Multiplexed Serum Biomarker Immunoassay Panel Discriminates Clinical Lung Cancer Patients from High-Risk Individuals Found to be Cancer-Free by CT Screening." Journal of Thoracic Oncology. Apr. 2012. vol. 7, No. 4. pp. 698-708.
Chen, Xi, et al. "Identification of ten serum microRNAs from a genome-wide serum microRNA expression profile as novel noninvasive biomarkers for nonsmall cell lung cancer diagnosis." International Journal of Cancer. 2012. vol. 130, No. 7. pp. 1620-1628.
Devos, Theo., et al. "Circulating Methylated SEPT9 DNA in Plasma is a Biomarker for Colorectal Cancer." Clinical chemistry, 2009. vol. 55, No. 7. pp. 1337-1346.
Farlow, Erin C., et al. "Development of a Multiplexed Tumor-Associated Autoantibody-Based Blood Test for the Detection of Non-Small Cell Lung Cancer." Clinical Cancer Research. Jun. 22, 2010. vol. 16, No. 13. pp. 3452-3462.
Guergova-Kuras, Mariana, et al. "Discovery of Lung Cancer Biomarkers by Profiling the Plasma Proteome with Monoclonal Antibody Libraries." Molecular & Cellular Proteomics, 2011. 10(12).
Hennessey, Patrick T., et al. "Serum microRNA Biomarkers for Detection of Non-Small Cell Lung Cancer." PLoS ONE. Feb. 2012. vol. 7, No. 2. pp. e32307 (6 pages).
Higgins, Gillian, et al. "Variant Ciz1 is a circulating biomarker for early-stage lung cancer." PNAS. Oct. 16, 2012. pp. E3128-E3135.
Izbizcka, Elzbieta et al. "Plasma Biomarkers Distinguish Non-small Cell Lung Cancer from Asthma and Differ in Men and Women" Cancer Genomics—Proteomics. 2012. vol. 9, No. 1. pp. 27-35.
Kutteh, William H., et al. "Multiples of the Median: An Alternative Method for Reporting Antiphospholipid Antibodies in Women With Recurrent Pregnancy Loss." Obstetrics & Gynecology. Nov. 1994. vol. 84, No. 5. pp. 311-815.
Lam, Stephen, et al. "EarlyCDT-Lung: An Immunobiomarker Test as an Aid to Early Detection of Lung Cancer." Cancer Prevention Research. 2011. vol. 4, No. 7. pp. 1126-1134.
Mor, Gil, et al. "Serum protein markers for early detection of ovarian cancer." PNAS. May 24, 2005. vol. 102, No. 21. pp. 7677-7682.
The National Lung Screening Trial Research Team. Reduced Lung-Cancer mortality with Low-Dose Computed Tomographic Screening. The New England Journal of Medicine. Aug. 4, 2011 vol. 365, No. 5. pp. 395-409.

(Continued)

*Primary Examiner* — Karla Dines
(74) *Attorney, Agent, or Firm* — 20/20 GeneSystems; Koren Anderson

(57) ABSTRACT

A method of data interpretation from a multiplex cancer assay is described. The aggregate normalized score from the assay is transformed to a quantitative risk score quantifying a human subject's increased risk for the presence of cancer as compared to the known prevalence of the cancer in the population before testing the subject.

22 Claims, 10 Drawing Sheets

(56) References Cited

OTHER PUBLICATIONS

Ng, E.K.O., et al. "Differential expression of microRNAs in plasma of patients with colorectal cancer: a potential market for colorectal cancer screening." Gut. 2009. vol. 58, No. 10. pp. 1375-1381.

Ostroff, Rachel M., et al. "Unlocking Biomarker Discovery: Large Scale Application of Aptamer Proteomic Technology for Early Detection of Lung Cancer." PLoS ONE Dec. 2010. vol. 5, No. 12. pp. e15003 (10 pages).

Palomaki, Gleen E. and Louis M. Neveux. "Using Multiples of the Median to Normalize Serum Protein Measurements." Clinical Chemical and Laboratory Medicine. 2001. vol. 39, No. 11. pp. 1137-1145.

Patnaik, Santosh K., et al. "MicroRNA Expression Profiles of Whole Blood in Lung Adenocarcinoma." PLoS ONE 2012. vol. 7, No. 9. pp. e46045 (12 pages).

Patz, Edward F., et al. "Panel of Serum Biomarkers for the Diagnosis of Lung Cancer." Journal of Clinical Oncology. Dec. 10, 2007. vol. 25, No. 35. pp. 5578-5583.

Pine, Sharon R., et al., "Increased Levels of Circulating Interleukin 6, Interleukin 8, C-Reactive Protein, and Risk of Lung Cancer." Journal of the National Cancer Institute. 2011. vol. 103, No. 14. pp. 1112-1122.

Shen, Jun, et al. "Plasma microRNAs as potential biomarkers for non-small-cell lung cancer." Lab Investigation. 2011. vol. 91, No. 4. pp. 579-587.

Spitz, Margaret R., et al. "A Risk Model for Prediction of Lung Cancer." Journal of the National Cancer Institute. 2007. vol. 99, No. 9. pp. 715-726.

Tammemagi, C. Martin, et al. "Lung Cancer Risk Prediction: Prostate, Lung, Colorectal and Ovarian Cancer Screening Trial Models and Validation." Journal of the National Cancer Institute. 2011. vol. 103, No. 13. pp. 1058-1068.

\* cited by examiner

FIGURE 1: RISK CATAGORIZATION TABLE

| Aggregate MoM Values "Composite Score" | Risk Identifier | Increased Likelihood of Having Lung Caner "Risk Score" |
|---|---|---|
| | | |
| >20 | Highest | 13.4 x |
| 15-20 | Intermediate High Risk | 5 x |
| 10-14 | Intermediate Risk | 2.1 x |
| 7-9 | Intermediate Low Risk | 0.7 x |
| ≤6 | Low Risk | 0.4 x |

FIGURE 2: Analysis of Development Stage Blood Samples

Table I: Analysis of Development Stage Blood Samples

|  | All Lung Cancer | Early Stage (I & II) | Late Stage (III & IV) | All Non-Cancer | Normal | Benign Lung Disorders | At Risk Smokers | Other Cancers |
|---|---|---|---|---|---|---|---|---|
| n | 371 | 207 | 107 | 652 | 449 | 203 | 352 | 145 |
| min | 3 | 3 | 3 | 3 | 3 | 3 | 3 | 2 |
| max | 2455 | 460 | 2455 | 232 | 111 | 232 | 111 | 228 |
| average | 54 | 39 | 98 | 10 | 10 | 11 | 9 | 17 |
| median | 15 | 13 | 21 | 7 | 7 | 7 | 7 | 8 |
| > 10.7 | 237 | 123 | 80 | 133 | 87 | 46 | 72 | 49 |
| <= 10.7 | 134 | 84 | 27 | 519 | 362 | 157 | 280 | 96 |
| Sensitivity | 64% | 59% | 75% |  |  |  |  | 34% |
| Specificity |  |  |  | 80% | 81% | 77% | 80% | 66% |

FIGURE 3: ROC ANALYSIS OF DEVELOPMENT SET
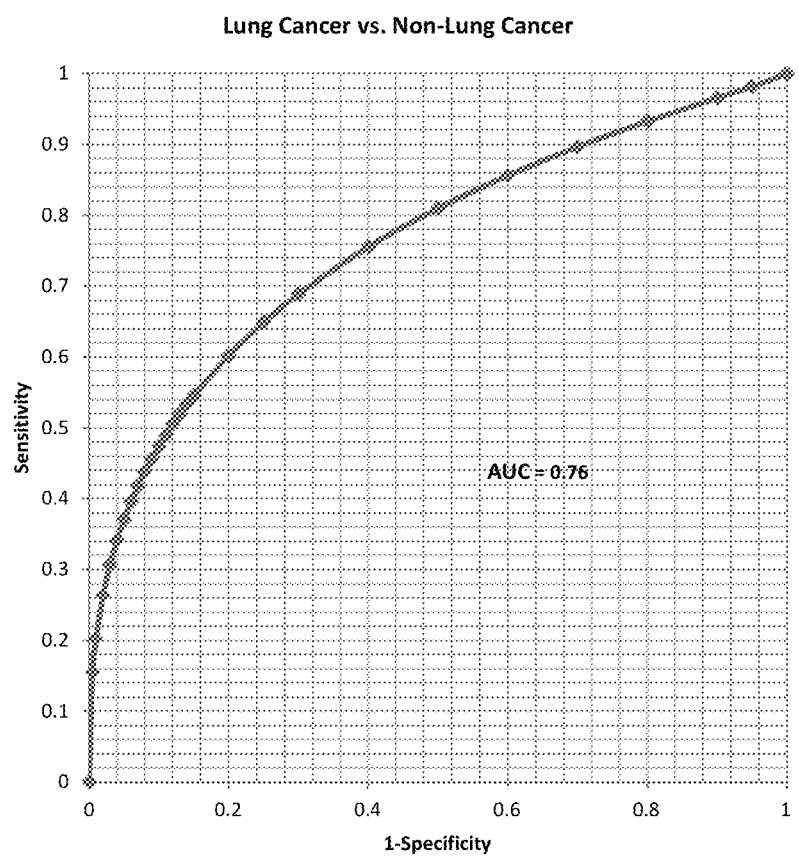

FIGURE 4: STATISTICAL FIRST VALIDATION COHORT

Table II: Statistics First Validation Cohort

|         | Cancer | Control |
|---------|--------|---------|
| n       | 97     | 225     |
| min     | 0.9    | 1.2     |
| max     | 307    | 347     |
| mean    | 35     | 10      |
| median  | 13     | 6       |
| > 10.7  | 55     | 46      |
| <= 10.7 | 42     | 179     |
| Sensitivity | 57% |       |
| Specificity |     | 80%   |

FIGURE 5: ROC CURVE FIRST VALIDATION COHORT
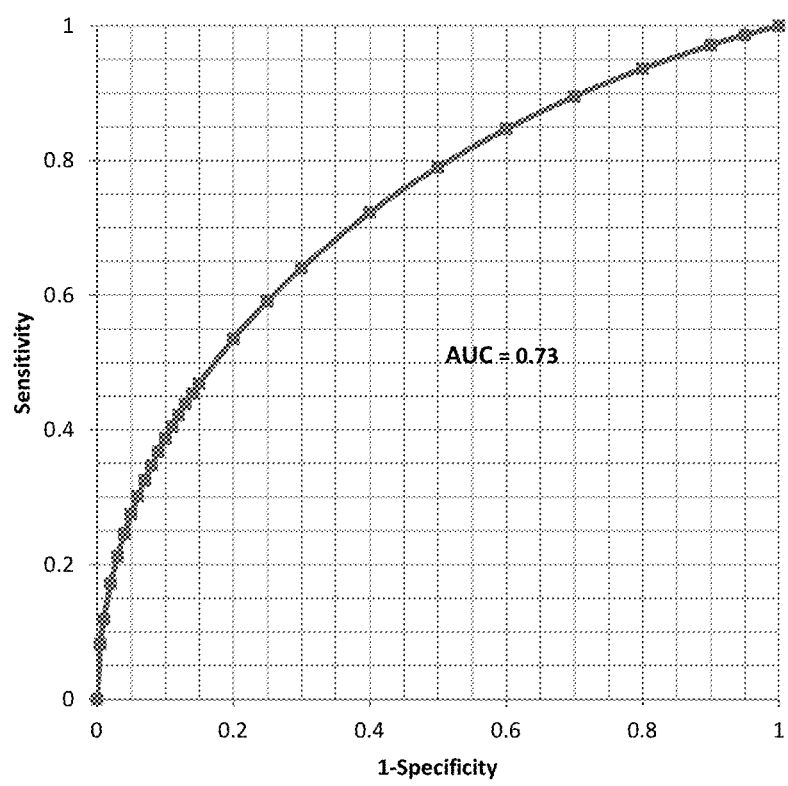

FIGURE 6: TUMOR MARKER LINERARITY
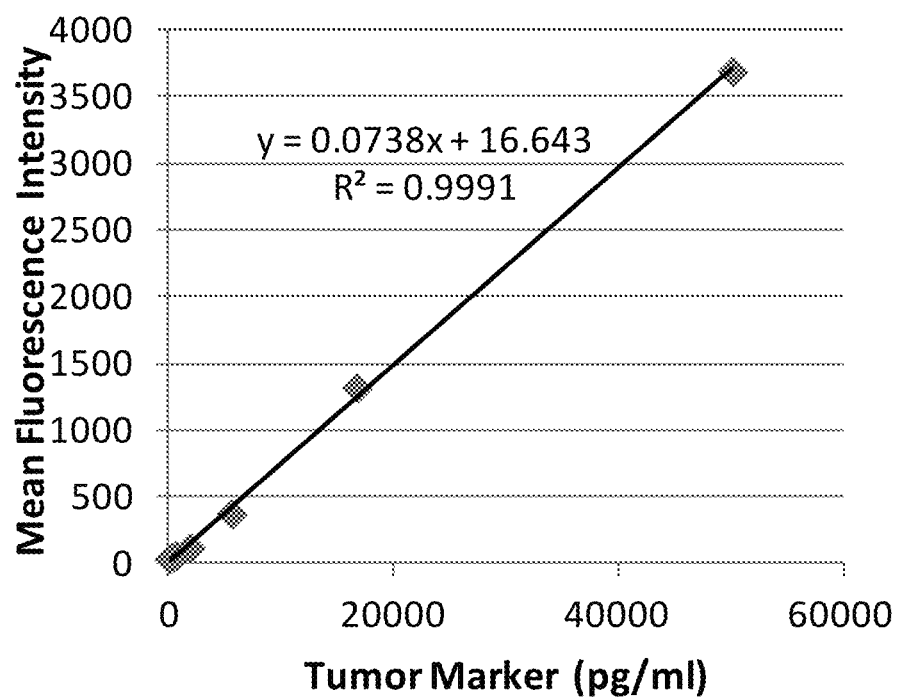

FIGURE 7: BIOMARKER PRECISION AND REPEATABILITY

|  | Marker 1 | | | Marker 2 | | | Marker 3 | | |
| --- | --- | --- | --- | --- | --- | --- | --- | --- | --- |
|  | Daily Mean | Repeatability (SD within run) | Precision (SD within laboratory) | Daily Mean | Repeatability (SD within run) | Precision (SD within laboratory) | Daily Mean | Repeatability (SD within run) | Precision (SD within laboratory) |
| Sample 1 | 240.1 | 8.8 | 27.7 | 91.6 | 1.8 | 10.6 | 43.8 | 1.0 | 7.6 |
| Sample 2 | 102.7 | 7.2 | 14.9 | 114.4 | 7.6 | 17.0 | 30.9 | 3.9 | 4.8 |
| Sample 3 | 77.9 | 6.2 | 12.0 | 56.7 | 3.7 | 17.4 | 24.4 | 2.5 | 3.4 |

FIGURE 8: FINAL VALIDATION STUDY
A:
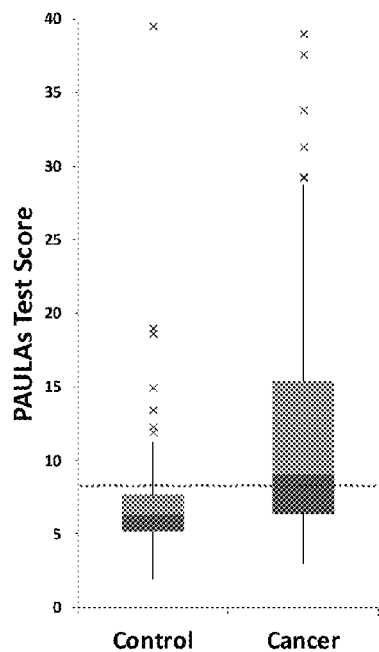
B:
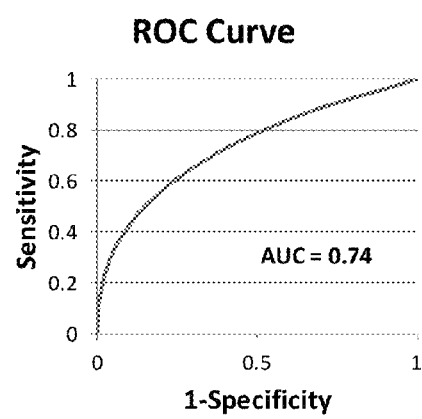
C:
|  | Control | Cancer |
|---|---|---|
| # samples | 121 | 134 |
| min | 1.94 | 2.97 |
| max | 39.53 | 179.10 |
| average | 6.98 | 15.38 |
| cutoff | 8.25 | 8.25 |
| above | 24 | 79 |
| Specificity | 80% | |
| Sensitivity | | 59% |

FIGURE 9: RESULTS OF USING LUNG CANCER ALGORITHM TO RECATEGORIZE AT-RISK

| Score | Interpretation | Sensitivity | Specificity | Accuracy | PPV | NPV | Cancer Found out of 20 | False Positives out of 980 |
|---|---|---|---|---|---|---|---|---|
| >20 | Highest Risk | 18.0% | 99.0% | 97.4% | 26.9% | 98.3% | 4 | 10 |
| >14 | Intermediate-High Risk | 29.0% | 97.0% | 95.6% | 16.5% | 98.5% | 6 | 29 |
| >9 | Intermediate Risk | 51.0% | 87.0% | 86.3% | 7.4% | 98.9% | 10 | 127 |
| >6 | Intermediate-Low Risk | 81.0% | 44.0% | 44.7% | 2.9% | 99.1% | 16 | 549 |
| All | Low Risk | 100.0% | 0.0% | 2.0% | 2.0% | N/A | 20 | 980 |

FIGURE 10: RESULTS OF USING LUNG CANCER ALGORITHM TO RECATEGORIZE AT-RISK

| Score | Interpretation | Sensitivity | Specificity | Accuracy | PPV | NPV | Cancer Found out of 20 | False Positives out of 980 |
|---|---|---|---|---|---|---|---|---|
| X>20 | Highest Risk | 18.0% | 99.0% | 97.4% | 26.9% | 98.3% | 4 | 10 |
| 14<X≤20 | Intermediate-High Risk | 11.0% | 98.0% | 95.6% | 10.1% | 98.2% | 2 | 20 |
| 9<X≤14 | Intermediate Risk | 22.0% | 90.0% | 86.3% | 4.3% | 98.3% | 4 | 98 |
| 6<X≤9 | Intermediate-Low Risk | 29.0% | 57.0% | 44.7% | 1.4% | 97.5% | 6 | 421 |
| X≤6 | Low Risk | 56.0% | 19.0% | 2.0% | 0.9% | 97.1% | 4 | 431 |

METHODS AND ALGORITHMS FOR AIDING IN THE DETECTION OF CANCER

CROSS REFERENCE TO RELATED APPLICATIONS

This applications claims the benefit under 35 U.S.C. 1.19(e) of U.S. Provisional Patent Application No. 61/577,083, filed Dec. 18, 2011, which is herein incorporated by reference in its entirety.

FIELD OF THE INVENTION

The disclosure relates to methods and algorithms for quantifying an increased risk for the presence of cancer in an asymptomatic human subject.

BACKGROUND OF THE INVENTION

Early Detection of Cancer

It is well established that for most cancers patient outcomes improve significantly if surgery and other therapeutic interventions commence before the tumor has metastasized. Accordingly many different techniques and technologies have been introduced into medical practice in an attempt to help physicians detect cancer early. These include various imaging modalities such as mammography as well as tests to identify cancer specific "biomarkers" in the blood and other bodily fluids such as the prostate specific antigen (PSA) test. The utility and value of many of these tests is often questioned particularly with regard to whether the costs and risks associated with false positives, false negatives, etc. outweighs the potential benefits in terms of actual lives saved.

Cancer detection poses significant technical challenges as compared to detecting infections since cancer cells, unlike viruses and bacteria, are biologically similar to and hard to distinguish from normal, healthy cells. For this reason tests used for the early detection of cancer often suffer from higher numbers of false positives and false negatives than comparable tests for viral or bacterial infections or for tests that measure genetic, enzymatic or hormonal abnormalities. This often causes confusion among healthcare practitioners and their patients leading in some cases to unnecessary, expensive, and invasive follow-on testing while in other cases a complete disregard for follow-up testing resulting in cancers detected too late for useful intervention. To be sure, physicians and patients welcome tests that yield a binary decision or result, either the patient is positive or negative for a condition, such as observed in the over the counter pregnancy test kits which present, for example, an immunoassay result in the shape of a plus sign or a negative sign as indication of pregnancy or not. However, unless the sensitivity and specificity of diagnosis approaches 99%, a level not obtainable for most cancer tests, such binary outputs can be highly misleading.

A need therefore exists for an approach or method that communicates to patients their relative risk of their having cancer that is clear and quantitative but avoids reporting results in "black or white" terms that can lead either to excessive worry or undue complacency. In this way, the risk of having a particular cancer can be defined in a way that allows a physician the ability to prioritize and target those higher risk patients in need of follow-up testing from those at lower risk. Such an approach would not only save lives and costs, but allows for a more personalized approach to screening and identifies those patients most likely to benefit from expensive and invasive follow-on testing. Primary care providers in particular typically see a high volume of patients per day and the demands of healthcare cost containment has dramatically shortened the amount of time they can spend with each patient. Accordingly they often lack sufficient time to take in depth family and lifestyle histories, to counsel patients on healthy lifestyles, or to follow-up with patients who have been recommended testing beyond that which is provided in their office practice.

It would, furthermore, be desirable that the aforementioned approach or method be more precise and accurate than mere epidemiological or lifestyle considerations. It is well known that factors such as age, family history, tobacco and alcohol use, diet and obesity impact the likelihood of having cancer in particular individuals. However, these factors alone provide, at best, a crude and subjective way for physicians to stratify the cancer risks among their patient population.

Others have provided algorithms wherein an individual can attempt to personalize their risk, without any testing, simply by providing relevant personal history such as age and their current smoking status. However, while these algorithms may be more accurate than relying on the reported rate of cancer in a particular group they do not take into account an individual's actual biological factors.

Thus, it would be desirable to provide a technique and method that overcomes the aforementioned limitations that quantifies an individual's risk as compared to their risk before testing.

Lung Cancer and Early Detection

Lung cancer is by far the leading cause of cancer deaths in North America and most of the world killing more people than the next three most lethal cancers combined, namely breast, prostate, and colorectal cancer. Lung cancer results in over 156,000 deaths per year in the United States alone (American Cancer Society. Cancer Facts & Figures 2011. *Atlanta: American Cancer Society;* 2011). Tobacco use has been identified as a primary causal factor for lung cancer and is thought to account for some 90% of cases. Thus, individuals over 50 years of age with a smoking history of greater than 20 pack-years have a 1 in 7 lifetime risk of developing the disease. Lung cancer is a relatively silent disease displaying few if any specific symptoms until it reaches the later more advanced stages. Therefore most patients are not diagnosed until their cancer has metastasized beyond the lung and they are no longer treatable by surgery alone. Thus, while the best way to prevent lung cancer is likely tobacco avoidance or cessation, for many current and former smokers, the transforming, cancer-causing event has already occurred and even though the cancer is not yet manifest, the damage is already done. Thus, perhaps the most effective means of reducing lung cancer mortality today is early stage detection when the tumor is still localized and amenable to surgery with intent to cure.

The importance of early detection was recently demonstrated in a large 7-year clinical study, the National Lung Cancer Screening Trial (NLST), which compared chest x-ray and chest CT scanning as potential modalities for the early detection of lung cancer (National Lung Screening Trial Research Team, Aberle D R, Adams A M, Berg C D, Black W C, Clapp J D, Fagerstrom R M, Gareen I F, Gatsonis C, Marcus P M, Sicks J D. *Reduced lung-cancer mortality with low-dose computed tomographic screening.* N Engl J. Med. 2011 Aug. 4; 365(5):395-409). The trial concluded that the use of chest CT scans to screen the at-risk population identified significantly more early stage lung cancers than chest x-ray and resulted in a 20% overall reduction in disease mortality. This study has clearly indicated that identifying lung cancer early can save lives. Unfortunately, the broad application of CT scanning as a screening method for lung cancer is not without problems. The NLST design utilized a serial CT screening paradigm in which patients received a CT scan annually for only three years. Nearly 40% of the participants receiving the annual CT scan over 3 years had at least one positive screening result and 96.4% of these positive screening results were false positives. This very high rate of false positives can cause patient anxiety and a burden on the healthcare system, as the work-up following a positive finding on low-dose CT scans often includes advanced imaging and biopsies. Although CT scanning is an important tool for the early detection of lung cancer, more than two years after the NLST results were announced, very few patients at high risk for lung cancer due to smoking history have initiated a program of annual CT scans. This reluctance to undergo yearly CT scans is likely due to a number of factors including costs, perceived risks of radiation exposure especially by serial CT scans, the inconvenience or burden to asymptomatic patients of scheduling a separate diagnostics procedure at a radiology center, as well as concerns by physicians that the very high false positive rates of CT scanning as a standalone test will result in a significant number of unnecessary follow up diagnostic tests and invasive procedures.

While the overall lifetime risk for lung cancer amongst smokers is high, the chance that any individual smoker has cancer at a specific point in time is only on the order of 1.5-2.7% [Bach, P. B., et al., Screening for Lung Cancer*ACCP Evidence-Based Clinical Practice Guidelines (2nd Edition). CHEST Journal, 2007. 132(3_suppl): p. 69S-77S.]. Due to this low disease prevalence, a simple method to better identify which patients are at highest risk is necessary. The ideal method would be non-invasive, highly accurate and easily performed in the context of the standard work-up of the patient at a yearly physician visit with the standard blood work-up. Such a test needs to have at least a moderate level of sensitivity and be amenable to serial testing with a high level of patient compliance. The best format for such a test that meets all of these requirements is a simple blood test.

It would be desirable to have such a blood test for lung cancer in, asymptomatic, at risk patients (including smokers and former smokers) wherein their risk for the presence of cancer is quantified in terms of an increase over others in the same risk population. Such a test would ideally help healthcare practitioners communicate to patients their relative risk of having cancer that is clear and quantitative but avoids absolute "yes or no" results associated with false positives or negatives which discourage patients from being tested on a routine basis.

It would also be desirable to have such a test that gives physicians the ability to prioritize and target those patients at the highest risk for lung cancer for advanced testing such as CT scans.

These and other advantages of the present invention may be better understood by referring to the following description, accompanying drawings and claims. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

SUMMARY OF THE INVENTION

The present invention relates generally to non-invasive methods and tests to help assess the likelihood that a patient has cancer relative to a wider patient population as a first step to determine whether that patient should be followed up with additional, more invasive cancer testing. It has now been discovered that by use of retrospect clinical samples (cancer and control) and a panel of biomarkers for cancer, asymptomatic patients can now have their risk for the presence of cancer quantified in terms of an increase over the population. It is now possible to produce meaningful information for physicians in at-risk, but asymptomatic, patient population groups that can be used to inform further screening procedures.

More specifically, the invention includes, for example, a blood test for assessing the likelihood that a patient has lung cancer relative to a population of individuals of a similar age range and smoking history. In this example, several biomarkers are analyzed from the patient's fluid sample, e.g., a blood sample, which leads to a composite score that is then compared to a database of composite scores from a wider population of patients known to have lung cancer as well as non-cancer controls. This permits the patients risk of having lung cancer to be categorized as low, intermediate, high, very high, etc. Armed with this information, physicians and other healthcare practitioners, their patients, and health insurance companies, can better determine which patients are most likely to benefit from follow-on testing including CT screening. Such a method reduces the costs, anxiety, and radiation exposure associated with having lower risk patients undergo CT scans while helping to ensure that patients at higher risks of having lung cancer undergo CT scanning in hopes of detecting their tumor at an early stage when they can still benefit from curative surgery.

BRIEF DESCRIPTION OF THE FIGURES

The numerous advantages of the present invention may be better understood by those skilled in the art by reference to the accompanying figures in which:

FIG. 1 shows an example of a Risk Categorization Table for lung cancer. In this risk categorization table, the inflection point between having a risk greater than the observed risk of smokers of 2% occurs with an aggregate MoM score of 9. With an aggregate score of 9 or less, that patient has a risk of lung cancer no greater than does any other heavy smoker not yet diagnosed. A MoM score greater than 9 indicates a greater risk of cancer or a higher likelihood of cancer as compared to the smoking population.

FIG. 2 shows a table of the distribution of patient samples analyzed, including patients with all stages of cancer, at risk populations and various other control groups including those with non-cancerous lung disorders and other cancers.

FIG. 3 shows a receiver operator characteristic (ROC) curve analysis of all lung cancer vs. all non-cancer samples yielded an area under the curve (AUC) of 0.76.

FIG. 4 shows, in table form, the statistical validation using a cohort of 322 samples obtained with the specific intent of early detection in the high risk population.

FIG. 5 shows the ROC curve analysis for the cohort of 322 samples with an AUC of 0.73.

FIG. 6 shows the linearity of one of the tumor markers in a spike and recovery assay.

FIG. 7 shows the biomarker precision and repeatability from a clinical bridging study in table form.

FIG. 8 shows results from a blinded retrospective study using the six lung cancer biomarker panel.

FIG. 9 shows, in table form, results from the lung cancer assay for at-risk subjects re-categorizing the patients risk for the presence of lung cancer.

FIG. 10 shows results from the lung cancer assay for at-risk subjects re-categorizing the patient's risk, based on a range of composite scores, for the presence of lung cancer.

DETAILED DESCRIPTION OF THE INVENTION

A) Introduction

The present invention provides a risk categorization of a population used to determine a quantified risk level for the presence of a cancer in an asymptomatic human subject. The method is preferably used as part of a blood test that measures multiple biomarkers in the blood. In certain embodiments, the risk categorization is herein referred to a risk categorization table. As used herein, the term "table" is used in its broadest sense to refer to a grouping of data into a format providing for ease of interpretation or presentation, this includes, but is not limited to a computer program, software application, table, sliding template (e.g., pinwheel), spreadsheet, etc. Thus, in one embodiment the risk categorization table is a grouping of stratified human subject populations. This stratification of human subjects is based on analysis of retrospective clinical samples from subjects having a cancer wherein the actual incidence of cancer, herein referred to as the "positive predictive score" is determined for each stratified grouping. As used herein, the analysis of retrospective clinical samples refers to measurement of markers in those samples, including normalization of values and summing those values to generate a risk score for each sample. The positive predictive score is then converted to a multiplier indicating increased likelihood of having the cancer by dividing the positive predictive score by the reported incidence of cancer in the cohort of the population subject to stratification, (e.g. human subjects 50 years or older). Each grouping is given a risk categorization indicator, including, but not limited to, low risk, intermediate-low risk, intermediate risk, intermediate-high risk and highest risk. Thus, in one embodiment, each category of the risk categorization table comprises 1) a multiplier indicating increased likelihood of having the cancer, 2) a risk identifier and 3) a range of composite scores.

It is understood that the basis for the stratification of a cohort of a population of human subjects is based on 1) an identification of a certain cancer and 2) biomarkers that are associated with the cancer. In other words, a cohort shares the same cancer risk factors. Validation of the biomarkers to be used in the present methods is provided by analyzing retrospective cancer samples along with age matched normal (non-cancer) samples.

The generation of a risk categorization table, including methods for normalizing biomarker data, is provided in more detail below along with a specific example for lung cancer.

The present invention further provides an algorithm for analyzing a panel of biomarkers for a cancer and quantifying a human subject's increased risk (or in certain circumstances decreased risk) for the presence of the cancer in an asymptomatic human subject relative to a population. As used herein, the term "increased risk" refers to an increase for the presence of the cancer as compared to the known prevalence of that particular cancer across the population cohort. The present methods are based on the generation of a risk categorization table for a certain cancer; wherein there is no intended limitation on when this table is generated just that when utilized the quantified risk is at the time of testing. Thus, the present method and risk categorization table is based, at least in part, on 1) the identification and clustering of a set of proteins and/or resulting autoantibodies to those proteins that can serve as markers for the presence of a cancer, 2) normalization and summing of the markers measured to generate a composite score; and, 3) determination of threshold values used to divide patients into groups with varying degrees of risk for the presence of cancer in which the likelihood of an asymptomatic human subject having a quantified increased risk for the presence of the cancer is determined. The algorithm yields a numerical risk score for each patient tested, which can be used by physicians to make treatment decisions concerning the therapy of cancer patients or, importantly, to further inform screening procedures to better predicted and diagnose early stage cancer in asymptomatic patients.

B) Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, the term "asymptomatic" refers to a patient or human subject that has not previously been diagnosed with the same cancer that their risk of having is now being quantified and categorized. For example, human subjects may shows signs such as coughing, fatigue, pain, etc., but had not been previously diagnosed with lung cancer but are now undergoing screening to categorize their increased risk for the presence of cancer and for the present methods are still considered "asymptomatic".

As used herein, the term "AUC" refers to the Area Under the Curve, for example, of a ROC Curve. That value can assess the merit of a test on a given sample population with a value of 1 representing a good test ranging down to 0.5 which means the test is providing a random response in classifying test subjects. Since the range of the AUC is only 0.5 to 1.0, a small change in AUC has greater significance than a similar change in a metric that ranges for 0 to 1 or 0 to 100%. When the % change in the AUC is given, it will be calculated based on the fact that the full range of the metric is 0.5 to 1.0. A variety of statistics packages can calculate AUC for an ROC curve, such as, JMP™ or Analyse-It™. AUC can be used to compare the accuracy of the classification algorithm across the complete data range. Classification algorithms with greater AUC have, by definition, a greater capacity to classify unknowns correctly between the two groups of interest (disease and no disease). The classification algorithm maybe as simple as the measure of a single molecule or as complex as the measure and integration of multiple molecules.

As used herein, the terms "biological sample" and "test sample" refer to all biological fluids and excretions isolated from any given subject. In the context of the present invention such samples include, but are not limited to, blood, blood serum, blood plasma, urine, tears, saliva, sweat, biopsy, ascites, cerebrospinal fluid, milk, lymph, bronchial and other lavage samples, or tissue extract samples. In certain embodiments, blood, serum, plasma and bronchial lavage or other liquid samples are convenient test samples for use in the context of the present methods.

As used herein, the terms "cancer" and "cancerous" refer to or describe the physiological condition in mammals that is typically characterized by unregulated cell growth. Examples of cancer include but are not limited to, lung cancer, breast cancer, colon cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

As used herein, the term "cancer risk factors" refers to biological or environmental influences that are known risks associated with a particular cancer. These cancer risk factors include, but are not limited to, a family history of cancer (e.g. breast cancer), age, weight, sex, history of smoking tobacco, exposure to asbestos, exposure to radiation, etc. It is understood that these cancer risk factors, either individually or a combination thereof, contribute to selecting a cohort of the population used to develop a Risk Categorization Table and that this same cohort is then tested using the present methods and algorithm to determine their increased risk for the presence of cancer as compared to the known prevalence of cancer across the cohort. In certain embodiments, cancer risk factors for lung cancer are a human subject aged 50 years or older with a history of smoking tobacco.

As used herein, the term "cohort" refers to a group or segment of human subjects with shared factors or influences, such as age, family history, cancer risk factors, environmental influences, etc. In one instance, as used herein, a "cohort" refers to a group of human subjects with shared cancer risk factors; this is also referred to herein as a "disease cohort". In another instance, as used herein, a "cohort" refers to a normal population group matched, for example by age, to the cancer risk cohort; also referred to herein as a "normal cohort".

As used herein, the term "composite score" refers to a summation of the normalized values for the predetermined markers measured in the sample from the human subject. In one embodiment, the normalized values are reported as a multiple of median (MoM) values and those MoM values are then summed to provide a composite score for each human subjected tested. When used in the context of the risk categorization table and correlated to a stratified grouping based on a range of composite scores in the Risk Categorization Table, the "composite score" is used to determine the "risk score" for each human subject tested wherein the multiplier indicating increased likelihood of having the cancer for the stratified grouping becomes the "risk score". See, FIG. 1.

In certain aspects the "cohort score" is also referred to herein as the "test score".

As used herein, the term "decision tree" refers to a classifier with a flow-chart-like tree structure employed for classification. Decision trees consist of repeated splits of a data set into subsets. Each split consists of a simple rule applied to one variable, e.g., "if value of 'variable 1' larger than 'threshold 1'; then go left, else go right". Accordingly, the given feature space is partitioned into a set of rectangles with each rectangle assigned to one class.

As used herein, the terms "differentially expressed gene," "differential gene expression" and their synonyms, which are used interchangeably, are used in the broadest sense and refers to a gene and/or resulting protein whose expression is activated to a higher or lower level in a subject suffering from a disease, specifically cancer, such as lung cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products (e,g, proteins), or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages.

As used herein, the term "gene expression profiling" is used in the broadest sense, and includes methods of quantification of mRNA and/or protein levels in a biological sample.

As used herein, the term "increased risk" refers to an increase in the risk level, for a human subject after testing, for the presence of a cancer relative to a population's known prevalence of a particular cancer before testing. In other words, a human subject's risk for cancer before testing may be 2% (based on the understood prevalence of cancer in the population), but after testing (based on the measure of biomarkers) their risk for the presence of cancer may be 30% or alternatively reported as an increase of 15 times compared to the cohort. The algorithm for calculating the 30% risk of having the cancer and the increased risk of 15 times the cohort population is provided in more detail below. It is also contemplated, as will be apparent from the present Risk Categorization Table and accompanying algorithm, that it is possible that the re-categorization of a patients risk for the presence of a cancer results in a risk that is less than the known prevalence of a particular cancer across a population cohort. For example, a human subjects risk for cancer before testing may be 2% (based on the understood prevalence of cancer in the population), but after testing (based on the measure of biomarkers) their risk for the presence of cancer may be 1% or alternatively reported as an increase of 0.5 times compared to the cohort. In this instance, "increased risk" refers to a change in risk level relative to a population before testing.

As used herein, the term "decreased risk" refers to a decrease in the risk level, for a human subject after testing, for the presence of a cancer relative to a population's known prevalence of a particular cancer before testing. In this instance, "decreased risk" refers to a change in risk level relative to a population before testing.

As used herein, the term "lung cancer" refers to a cancer state associated with the pulmonary system of any given subject. In the context of the present invention, lung cancers include, but are not limited to, adenocarcinoma, epidermoid carcinoma, squamous cell carcinoma, large cell carcinoma, small cell carcinoma, non-small cell carcinoma, and bronchoalveolar carcinoma. Within the context of the present invention, lung cancers may be at different stages, as well as varying degrees of grading. Methods for determining the stage of a lung cancer or its degree of grading are well known to those skilled in the art.

As used herein, the terms "marker", "biomarker" (or fragment thereof) and their synonyms, which are used interchangeably, refer to molecules that can be evaluated in a sample and are associated with a physical condition. For example, a markers include expressed genes or their products (e.g. proteins) or autoantibodies to those proteins that can be detected from a human samples, such as blood, serum, solid tissue, and the like, that, that is associated with a physical or disease condition. Such biomarkers include, but are not limited to, biomolecules comprising nucleotides, amino acids, sugars, fatty acids, steroids, metabolites, polypeptides, proteins (such as, but not limited to, antigens and antibodies), carbohydrates, lipids, hormones, antibodies, regions of interest which serve as surrogates for biological molecules, combinations thereof (e.g., glycoproteins, ribonucleoproteins, lipoproteins) and any complexes involving any such biomolecules, such as, but not limited to, a complex formed between an antigen and an autoantibody that binds to an available epitope on said antigen. The term "biomarker" can also refer to a portion of a polypeptide (parent) sequence that comprises at least 5 consecutive amino acid residues, preferably at least 10 consecutive amino acid residues, more preferably at least 15 consecutive amino acid residues, and retains a biological activity and/or some functional characteristics of the parent polypeptide, e.g. antigenicity or structural domain characteristics. The present markers refer to both tumor antigens present on or in cancerous cells or those that have been shed from the cancerous cells into bodily fluids such as blood or serum. The present markers, as used herein, also refer to autoantibodies produced by the body to those tumor antigens. In one aspect, a "marker" as used herein refers to both tumor antigens and autoantibodies that are capable of being detected in serum of a human subject. It is also understood in the present methods that use of the markers in a panel may each contribute equally to the composite score or certain biomarkers may be weighted wherein the markers in a panel contribute a different weight or amount to the final composite score.

As used herein, the term "multiplier indicating increased likelihood of having the cancer" refers to a numerical value of the risk categorization table and assigned to a patient sample after testing quantifying that patients increased risk, above the cohort population, for the presence of a cancer. When used in the context of the risk categorization table when testing a human subject and correlated to a range of composite scores, the "multiplier indicating increased likelihood of having the cancer" becomes the "risk score" for each human subject tested. See, FIG. 1.

As used herein, the terms "multiple of median" or "MoM" refers to a measure of how far an individual test result deviates from the median. In the present method a predetermined marker is measured in a sample from an asymptomatic subject and the value is normalized as a multiple of median score.

As used herein, the term "normalization" and its derivatives, when used in conjunction with measurement of biomarkers across samples and time, refer to mathematical methods where the intention is that these normalized values allow the comparison of corresponding normalized values from different datasets in a way that eliminates or minimizes differences and gross influences. In one embodiment, multiple of median is used as the normalization methodology for the present methods.

As used herein, the terms "panel of markers", "panel of biomarkers" and their synonyms, which are used interchangeably, refer to more than one marker that can be detected from a human sample that together, are associated with the presence of a particular cancer. In an embodiment of the present application, the presence of the biomarkers are not individually quantified as an absolute value to indicate the presence of a cancer, but the measured values are normalized and the normalized value is summed to provide a composite score. As disclosed above, each marker in the panel may be given the weight of 1, or some other value that is either a fraction of 1 or a multiple of 1, depending on the contribution of the marker to the cancer being screened and the overall composition of the panel.

As used herein, the term "pathology" of (tumor) cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the term "known prevalence of cancer" refers to a prevalence of a cancer in a population before the human subject is tested using the present methods. This known prevalence of cancer, can be a prevalence reported in the literature based on retrospective data or an algorithm applied to that prevalence where in the algorithm takes into account factors such as age and more immediate and relevant history. In this instance, a known prevalence of cancer in a cohort refers to a risk of having cancer prior to being tested by the present methods.

As used herein, the term "a positive predictive score," "a positive predictive value," or "PPV" refers to the likelihood that a score within a certain range on a biomarker test is a true positive result. It is defined as the number of true positive results divided by the number of total positive results. True positive results can be calculated by multiplying the test Sensitivity times the Prevalence of disease in the test population. False positives can be calculated by multiplying (1 minus the Specificity) times (1−the prevalence of disease in the test population). Total positive results equal True Positives plus False Positivies.

As used herein, the term "risk score" refers to a single numerical value that indicates an asymptomatic human subject's increased risk for the presence of a cancer as compared to the known prevalence of cancer in the disease cohort. In certain embodiments of the present methods, the composite score as calculated for a human subject and correlated to a multiplier indicating increased likelihood of having the cancer, wherein the composite score is correlated based on the range of composite scores for each stratified grouping in the risk categorization table. In this way the composite score is converted to a risk score based on the multiplier indicating increased likelihood of having the cancer for the grouping that is the best match for the composite score. See, FIG. 1.

As used herein the term, "Receiver Operating Characteristic Curve," or, "ROC curve," is a plot of the performance of a particular feature for distinguishing two populations, patients with lung cancer, and controls, e.g., those without lung cancer. Data across the entire population (namely, the patients and controls) are sorted in ascending order based on the value of a single feature. Then, for each value for that feature, the true positive and false positive rates for the data are determined. The true positive rate is determined by counting the number of cases above the value for that feature under consideration and then dividing by the total number of patients. The false positive rate is determined by counting the number of controls above the value for that feature under consideration and then dividing by the total number of controls.

ROC curves can be generated for a single feature as well as for other single outputs, for example, a combination of two or more features that are combined (such as, added, subtracted, multiplied etc.) to provide a single combined value which can be plotted in a ROC curve.

The ROC curve is a plot of the true positive rate (sensitivity) of a test against the false positive rate (1-specificity) of the test. ROC curves provide another means to quickly screen a data set.

As used herein, the term "screening" refers to a strategy used in a population to identify an unrecognized cancer in asymptomatic subjects, for example those without signs or symptoms of the cancer. As used herein, a cohort of the population (e.g. smokers aged 50 or older) are screened for a particular cancer (e.g. lung cancer) wherein the present algorithm is applied to determine the quantified increased risk to those asymptomatic subjects for the presence of the cancer.

As used herein, the term "subject" refers to an animal, preferably a mammal, including a human or non-human. The terms "patient" and "human subject" may be used interchangeably herein.

As used herein, the term "tumor," refers to all neoplastic cell growth and proliferation, whether malignant or benign, and all pre-cancerous and cancerous cells and tissues.

As used herein, the phrase "Weighted Scoring Method" refers to a method that involves converting the measurement of one biomarker that is identified and quantified in a test sample into one of many potential scores. A ROC curve can be used to standardize the scoring between different markers by enabling the use of a weighted score based on the inverse of the false positive % defined from the ROC curve. The weighted score can be calculated by multiplying the AUC by a factor for a marker and then dividing by the false positive % based on a ROC curve. The weighted score can be calculated using the formula:

$$\text{Weighted Score} = (AUC_x \times \text{factor}) / (1 - \% \text{ specificity}_x)$$

wherein x is the marker; the, "factor," is a real number (such as 0, 1, 2, 3, 4, 5, 6, 7, 8, 9, 10, 11, 12, 13, 14, 15, 16, 17, 18, 19, 20, 21, 22, 23, 24, 25 and so on) throughout the panel; and the, "specificity," is a chosen value that does not exceed 95%. Multiplication of a factor for the panel allows the user to scale the weighted score. Hence, the measurement of one marker can be converted into as many or as few scores as desired.

The weighting provides higher scores for biomarkers with a low false positive rate (thereby having higher specificity) for the population of interest. The weighting paradigm can comprise electing levels of false positivity (1-specificity) below which the test will result in an increased score. Thus, markers with high specificity can be given a greater score or a greater range of scores than markers that are less specific.

Foundation for assessing the parameters for weighing can be obtained by determining presence of a marker in a population of patients with lung cancer and in normal individuals. The information (data) obtained from all the samples are used to generate a ROC curve and to create an AUC for each biomarker. A number of predetermined cutoffs and a weighted score are assigned to each biomarker based on the % specificity. That calculus provides a stratification of aggregate scores, and those scores can be used to define ranges that correlate to arbitrary risk categories of whether one has a higher or lower risk of having lung cancer. The number of categories can be a design choice or may be driven by the data.

C) Methods for Determining a Quantified Risk Level for the Presence of a Cancer in an Asymptomatic Human In certain embodiments, provided herein are methods for quantifying the risk level of an asymptomatic patient relative to a population. In one aspect, the risk level is increased as compared to the population. In another aspect, the risk level is decreased as compared to the population. The asymptomatic patients that, after testing, have a quantified increased risk for the presence of cancer relative to the population are those that a physician may select for follow-on testing and it is important to not only know that their risk is increased, relative to the population, but that their risk is quantified.

Therefore, in certain embodiments, the method of determining a quantified increased risk for the presence of a cancer in an asymptomatic human subject, comprises 1) measuring a panel of markers in a sample from the human subject; 2) determining a normalized value of each marker in a sample from a human subject; 3) summing the normalized value to obtain a composite score for the human subject; 4) quantifying the increased risk for the presence of the cancer for the human subject as a risk score, wherein the composite score is matched to a risk category of a grouping of stratified human subject populations wherein each risk category comprises a multiplier indicating increased likelihood of having the cancer correlated to a range of composite scores; and, 5) providing a risk score for the human subject, whereby the quantified increased risk for the presence of a cancer in an asymptomatic human subject has been determined.

One or more steps of the method described herein can be performed manually or can be completely or partially automated (for example, one or more steps of the method can be performed by a computer program or algorithm. If the method were to be performed via computer program or algorithm, then the performance of the method would further necessitate the use of the appropriate hardware, such as input, memory, processing, display and output devices, etc). Methods for automating one or more steps of the method would be well within the skill of those in the art.

In yet further embodiments, the present invention contemplates specific use computer, which may be a general purpose computer, configured to perform the steps of the method described herein. The method, or portions of the method, may be further embodied in a computer readable medium capable of being executed in a computer environment. Such computer readable medium may be a specific storage device, such as a disk, or a location on a server, physical or virtual, the may be accessed by a computer for performing the required steps of the method.

i) Measuring Markers in a Sample

The first step in the present method is measuring a panel of markers from an asymptomatic human subject. There are many methods known in the art for measuring either gene expression (e.g. mRNA) or the resulting gene products (e.g. polypeptides or proteins) that can be used in the present methods.

The method of interest is not limited to any one assay format or to any particular set of markers that comprise a panel. For example, PCT International Pat. Pub. No. WO 2009/006323; US Pub. No. 2012/0071334; US Pat. Pub. No. 2008/0160546; US Pat. Pub. No. 2008/0133141; US Pat. Pub. No. 2007/0178504 (each herein incorporated by reference) teaches a multiplex lung cancer assay using beads as the solid phase and fluorescence or color as the reporter in an immunoassay format. Hence, the degree of fluorescence or color can be provided in the form of a qualitative score as compared to an actual quantitative value of reporter presence and amount.

For example, the presence and quantification of one or more antigens or antibodies in a test sample can be determined using one or more immunoassays that are known in the art. Immunoassays typically comprise: (a) providing an antibody (or antigen) that specifically binds to the biomarker (namely, an antigen or an antibody); (b) contacting a test sample with the antibody or antigen; and (c) detecting the presence of a complex of the antibody bound to the antigen in the test sample or a complex of the antigen bound to the antibody in the test sample.

Well known immunological binding assays include, for example, an enzyme linked immunosorbent assay (ELISA), which is also known as a "sandwich assay", an enzyme immunoassay (EIA), a radioimmunoassay (RIA), a fluoroimmunoassay (FIA), a chemiluminescent immunoassay (CLIA) a counting immunoassay (CIA), a filter media enzyme immunoassay (META), a fluorescence-linked immunosorbent assay (FLISA), agglutination immunoassays and multiplex fluorescent immunoassays (such as the Luminex Lab MAP), immunohistochemistry, etc. For a review of the general immunoassays, see also, Methods in Cell Biology: Antibodies in Cell Biology, volume 37 (Asai, ed. 1993); Basic and Clinical Immunology (Daniel P. Stites; 1991).

The immunoassay can be used to determine a test amount of an antigen in a sample from a subject. First, a test amount of an antigen in a sample can be detected using the immunoassay methods described above. If an antigen is present in the sample, it will form an antibody-antigen complex with an antibody that specifically binds the antigen under suitable incubation conditions described above. The amount of an antibody-antigen complex can be determined by comparing the measured value to a standard or control. The AUC for the antigen can then be calculated using techniques known, such as, but not limited to, a ROC analysis.

In another embodiment, gene expression of markers (e.g. mRNA) is measured in a sample from a human subject. For example, gene expression profiling methods for use with paraffin-embedded tissue include quantitative reverse transcriptase polymerase chain reaction (qRT-PCR), however, other technology platforms, including mass spectroscopy and DNA microarrays can also be used. These methods include, but are not limited to, PCR, Microarrays, Serial Analysis of Gene Expression (SAGE), and Gene Expression Analysis by Massively Parallel Signature Sequencing (MPSS).

Any methodology that provides for the measurement of a marker or panel of markers from a human subject is contemplated for use with the present methods. In certain embodiments, the sample from human subject is a tissue section such as from a biopsy. In another embodiment, the sample from the human subject is a bodily fluid such as blood, serum, plasma or a part or fraction thereof. In other embodiments, the sample is a blood or serum and the markers are proteins measured there from. In yet another embodiment, the sample is a tissue section and the markers are mRNA expressed therein. Many other combinations of sample forms from the human subjects and the form of the markers are contemplated.

ii) Biomarkers

However, before measurement can be performed a panel of markers needs to be selected for a particular cancer being screened. Many markers are known for cancers and a known panel can be selected, or as was done by the present Applicants, a panel can be selected based on measurement of individual markers in retrospective clinical samples wherein a panel is generated based on empirical data for a desired cancer.

Examples of biomarkers that can be employed include molecules detectable, for example, in a body fluid sample, such as, antibodies, antigens, small molecules, proteins, hormones, genes and so on.

In a particular embodiment, a panel of markers is selected based on their association with lung cancer. In one embodiment, the panel of markers is selected from anti-p53, anti-NY-ESO-1, anti-ras, anti-Neu, anti-MAPKAPK3, cytokeratin 8, cytokeratin 19, cytokeratin 18, CEA, CA125, CA15-3, CA19-9, Cyfra 21-1, serum amyloid A, proGRP and $\alpha_1$-antitrypsin (US 20120071334; US 20080160546; US 20080133141; US 20070178504 (each herein incorporated by reference)). Many circulating proteins have more recently been identified as possible biomarkers for the occurrence of lung cancer, for example the proteins CEA, RBP4, hAAT, SCCA [Patz, E. F., et al., Panel of Serum Biomarkers for the Diagnosis of Lung Cancer. Journal of Clinical Oncology, 2007. 25(35): p. 5578-5583.]; the proteins IL6, IL-8 and CRP [Pine, S. R., et al., Increased Levels of Circulating Interleukin 6, Interleukin 8, C-Reactive Protein, and Risk of Lung Cancer. Journal of the National Cancer Institute, 2011. 103(14): p. 1112-1122.]; the proteins TNF-a, CYFRA 21-1, IL-1ra, MMP-2, monocyte chemotactic protein-1 & sE-selectin [Farlow, E. C., et al., Development of a Multiplexed Tumor-Associated Autoantibody-Based Blood Test for the Detection of Non-Small Cell Lung Cancer. Clinical Cancer Research, 2010. 16(13): p. 3452-3462.]; the proteins prolactin, transthyretin, thrombospondin-1, E-selectin, C—C motif chemokine 5, macrophage migration inhibitory factor, plasminogen activator inhibitor, receptor tyrosine-protein kinase, erbb-2, cytokeratin fragment 21.1, and serum amyloid A [Bigbee, W. L. P., et al., —A Multiplexed Serum Biomarker Immunoassay Panel Discriminates Clinical Lung Cancer Patients from High-Risk Individuals Found to be Cancer-Free by CT Screening [Journal of Thoracic Oncology April, 2012. 7(4): p. 698-708.]; the proteins EGF, sCD40 ligand, IL-8, MMP-8 [Izbicka, E., et al., Plasma Biomarkers Distinguish Non-small Cell Lung Cancer from Asthma and Differ in Men and Women. Cancer Genomics—Proteomics, 2012. 9(1): p. 27-35.].

Novel ligands that bind to circulating, lung-cancer associated proteins which are possible biomarkers include nucleic acid aptamers to bind cadherin-1, CD30 ligand, endostatin, HSP90α, LRIG3, MIP-4, pleiotrophin, PRKCI, RGM-C, SCF-sR, sL-selectin, and YES [Ostroff, R. M., et al., Unlocking Biomarker Discovery: Large Scale Application of Aptamer Proteomic Technology for Early Detection of Lung Cancer. PLoS ONE, 2010. 5(12): p. e15003.] and monoclonal antibodies that bind leucine-rich alpho-2 glycoprotein 1 (LRG1), alpha-1 antichymotrypsin (ACT), complement C9, haptoglobin beta chain [Guergova-Kuras, M., et al., Discovery of Lung Cancer Biomarkers by Profiling the Plasma Proteome with Monoclonal Antibody Libraries. Molecular & Cellular Proteomics, 2011. 10(12).]; and the protein [Higgins, G., et al., Variant CizI is a circulating biomarker for early-stage lung cancer. Proceedings of the National Academy of Sciences, 2012.].

Autoantibodies that are proposed to be circulating markers for lung cancer include p53, NY-ESO-1, CAGE, GBU4-5, Annexin 1, and SOX2 [Lam, S., et al., EarlyCDT-Lung: An Immunobiomarker Test as an Aid to Early Detection of Lung Cancer. Cancer Prevention Research, 2011. 4(7): p. 1126-1134.] and IMPDH, phosphoglycerate mutase, ubiquillin, Annexin I, Annexin II, and heat shock protein 70-9B (HSP70-9B) [Farlow, E. C., et al., Development of a Multiplexed Tumor-Associated Autoantibody-Based Blood Test for the Detection of Non-Small Cell Lung Cancer. Clinical Cancer Research, 2010. 16(13): p. 3452-3462.].

Micro-RNAs that are proposed to be circulating markers for lung cancer include miR-21, miR-126, miR-210, miR-486-5p [Shen, J., et al., Plasma microRNAs as potential biomarkers for non-small-cell lung cancer. Lab Invest, 2011. 91(4): p. 579-587.]; miR-15a, miR-15b, miR-27b, miR-142-3p, miR-301 [Hennessey, P. T., et al., Serum microRNA Biomarkers for Detection of Non-Small Cell Lung Cancer. PLoS ONE, 2012. 7(2): p. e32307.]; let-7b, let-7c, let-7d, let-7e, miR-10a, miR-10b, miR-130b, miR-132, miR-133b, miR-139, miR-143, miR-152, miR-155, miR-15b, miR-17-5p, miR-193, miR-194, miR-195, miR-196b, miR-199a*, miR-19b, miR-202, miR-204, miR-205, miR-206, miR-20b, miR-21, miR-210, miR-214, miR-221, miR-27a, miR-27b, miR-296, miR-29a, miR-301, miR-324-3p, miR-324-5p, miR-339, miR-346, miR-365, miR-378, miR-422a, miR-432, miR-485-3p, miR-496, miR-497, miR-505, miR-518b, miR-525, miR-566, miR-605, miR-638, miR-660, and miR-93 [United States Patent Application 20110053158]; hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p and hsa-miR-324-3p. [United States Patent Application 20120108462]; miR-20a, miR-24, miR-25, miR-145, miR-152, miR-199a-5p, miR-221, miR-222, miR-223, miR-320 [Chen, X., et al., Identification of ten serum microRNAs from a genome-wide serum microRNA expression profile as novel noninvasive biomarkers for nonsmall cell lung cancer diagnosis. International Journal of Cancer, 2012. 130(7): p. 1620-1628.]; hsa-let-7a, hsa-let-7b, hsa-let-7d, hsa-miR-103, hsa-miR-126, hsa-miR-133b, hsa-miR-139-5p, hsa-miR-140-5p, hsa-miR-142-3p, hsa-miR-142-5p, hsa-miR-148a, hsa-miR-148b, hsa-miR-17, hsa-miR-191, hsa-miR-22, hsa-miR-223, hsa-miR-26a, hsa-miR-26b, hsa-miR-28-5p, hsa-miR-29a, hsa-miR-30b, hsa-miR-30c, hsa-miR-32, hsa-miR-328, hsa-miR-331-3p, hsa-miR-342-3p, hsa-miR-374a, hsa-miR-376a, hsa-miR-432-staR, hsa-miR-484, hsa-miR-486-5p, hsa-miR-566, hsa-miR-92a, hsa-miR-98 [Bianchi, F., et al., A serum circulating miRNA diagnostic test to identify asymptomatic high-risk individuals with early stage lung cancer. EMBO Molecular Medicine, 2011. 3(8): p. 495-503.] miR-190b, miR-630, miR-942, and miR-1284 [Patnaik, S. K., et al., MicroRNA Expression Profiles of Whole Blood in Lung Adenocarcinoma. PLoS ONE, 2012. 7(9): p. e46045.].

In one embodiment, a panel of markers for lung cancer is selected from CEA (GenBank Accession CAE75559), CA125 (UniProtKB/Swiss-Prot: Q8WXI7.2), Cyfra 21-1 (NCBI Reference Sequence: NP_008850.1), anti-NY-ESO-1 (antigen NCBI Reference Sequence: NP_001318.1), anti-p53 (antigen GenBank: BAC16799.1) and anti-MAP-KAPK3 (antigen NCBI Reference Sequence: NP_001230855.1), the first three are tumor marker proteins and the last three are autoantibodies.

In a certain embodiments, a panel of markers comprises circulating markers associated with colorectal cancer (CRC); those include the microRNA miR-92 [Ng, E. K. O., et al., Differential expression of microRNAs in plasma of patients with colorectal cancer: a potential marker for colorectal cancer screening. Gut, 2009. 58(10): p. 1375-1381.]; aberrantly methylated SEPT9 DNA [deVos, T., et al., Circulating Methylated SEPT9 DNA in Plasma Is a Biomarker for Colorectal Cancer. Clinical Chemistry, 2009. 55(7): p. 1337-1346.]

In certain embodiments, a panel of markers comprises markers associated with a cancer selected from bile duct cancer, bone cancer, pancreatic cancer, cervical cancer, colon cancer, colorectal cancer, gallbladder cancer, liver or hepatocellular cancer, ovarian cancer, testicular cancer, lobular carcinoma, prostate cancer, and skin cancer or melanoma. In other embodiments, a panel of markers comprises markers associated with breast cancer.

A panel can comprise any number of markers as a design choice, seeking, for example, to maximize specificity or sensitivity of the assay. Hence, an assay of interest may ask for presence of at least one of two or more biomarkers, three or more biomarkers, four or more biomarkers, five or more biomarkers, six or more biomarkers, seven or more biomarkers, eight biomarkers or more as a design choice.

Thus, in one embodiment, the panel of biomarkers may comprise at least two, at least three, at least four, at least five, at least six, at least seven, at least eight, at least nine or at least ten or more different markers. In one embodiment, the panel of biomarkers comprises about two to ten different markers. In another embodiment, the panel of biomarkers comprises about four to eight different markers. In yet another embodiment, the panel of markers comprises about six different markers.

Generally, a sample is committed to the assay and the results can be a range of numbers reflecting the presence and level of presence of each of the biomarkers of the panel in the sample.

The choice of the markers may be based on the understanding that each marker, when measured and normalized, contributed equally to determine the likelihood of the presence of the cancer. Thus in certain embodiments, the each marker in the panel is measured and normalized wherein none of the markers are given any specific weight. In this instance each marker has a weight of 1.

In other embodiments, the choice of the markers may be based on the understanding that each marker, when measured and normalized, contributed unequally to determine the likelihood of the presence of the cancer. In this instance, a particular marker in the panel can either be weighted as a fraction of 1 (for example if the relative contribution is low), a multiple of 1 (for example if the relative contribution is high) or as 1 (for example when the relative contribution is neutral compared to the other markers in the panel). Thus, in certain embodiments, the present methods further comprising weighting the normalized values prior to summation of the normalized values to obtain a composite score.

Decision tree is a data handling approach where a series of simple dichotomous decisions guide through a classification to yield such a desired binary outcome. Hence, samples are partitioned based on whether values thereof are above or below calculated thresholds.

A model for scoring multiple biomarkers which attempts to employ a decision tree logic was developed by Mor et al., PNAS, 102(21):7677-7682 (2005), wherein an optimal cut-off value is obtained and assigns a value of 0 (not likely to have cancer) or 1 (likely to have cancer) for a marker. Then, scores of individual biomarkers are combined for a final score of each sample and the higher the final score, the higher the probability of disease.

That technique provides a binary result favored by physicians and patients. While distribution of data is not an assumption which contributes to simplicity of the model, that the model reduces information to a 1 or 0 score results in a loss of quantitative information, for example, diminishes the role of a more predictive marker and elevates the role of a less predictive marker.

Moreover, the collection of markers in a multiplex assay may comprise varying levels of value or predictability in diagnosing disease. Hence, the impact of any one marker on the ultimate determination may be weighted based on the aggregated data obtained in screening populations and correlating with actual pathology to provide a more discriminating or effective diagnostic assay.

An alternative approach is to find an intermediate ground by expanding the qualitative transformation of quantitative data into multiple categories as compared to only a binary classification scheme.

a) Lung Cancer Biomarkers

One embodiment is directed to a method for assessing risk of lung cancer. A research effort to identify panels of biomarkers that included a survey of known tumor protein biomarkers coupled with a discovery project for novel lung cancer specific biomarkers was previously conducted (PCT Publ. No. 2009/006323, incorporated herein by reference). This work indicates although a combination of markers can be used to increase sensitivity of testing for cancer without greatly affecting the specificity of the test. To accomplish this, markers were tested and analyzed in a way that is often very different from the standard methods. This effort culminated in the establishment of a panel of six biomarkers that in the aggregate yield significant sensitivity and specificity for the early detection of lung cancer using the present methods. As disclosed herein, Applicants provide a new method and algorithm that can be utilized to identify smokers at the highest levels of risk for follow-up testing by CT scanning.

In certain embodiments, the lung cancer biomarker panel comprises a series of three tumor marker proteins and three autoantibodies. Tumor markers, in such embodiments, are proteins released by the cancer itself into the patient's serum. Since the presence of these proteins or their increased expression is directly related to the cancer cells they tend to be specific to cancer, however they may often be found in more than one type of cancer. Furthermore, because they are derived directly from the tumor, their levels will depend on the size of the tumor. This can make them less sensitive for the detection of early stage cancers. Autoantibodies are a function of the patient's immune response to the abnormal cancerous cells. Because the immune system amplifies its response even to a small amount of antigen, autoantibodies may be detected more easily in the early stage patient than proteins released by the cancer itself. Unfortunately due to the heterogeneity of the cancers we classify as lung cancer and the individual differences in patient immune responses, a large panel of autoantibodies is required to sensitively detect all lung cancers. Our panel combines both tumor markers and autoantibodies to achieve the greatest sensitivity for early stage lung cancer.

In certain embodiments, the tumor markers incorporated into the present methods for lung cancer comprise CEA, CA-125 and Cyfra 21-1. All three of these markers have been extensively studied by others and are currently in clinical use for monitoring of other cancers. While none of these markers have fared well as a stand-alone marker for the early detection of lung cancer, two important points must be iterated; 1) these markers are not measured by the present method in the same way they have been measured in the past for other indications, and 2) these markers are not deployed as stand-alone markers but rather are incorporated as a part of an integrated panel of markers for re-stratification of patient risk. Specifically, results in the present methods for lung cancer are not based on an absolute serum level, but on an increase in level as compared to the median levels in matched control patients. As such, individual marker values as a total serum concentration are not measured; instead these three markers are incorporated in a composite score that has value only in re-categorizing patient risk for the presence of lung cancer.

In certain embodiments, three autoantibodies are utilized in the present lung cancer test, wherein the autoantibodies comprise anti-p53, anti-NY-ESO-1 and anti-MAPKAPK3. As noted above, most autoantibodies are only found in a limited number of patients. These three autoantibodies are among those most commonly found in lung cancer, although each on its own has a rather limited distribution as members of an integrated biomarker panel because they do contribute to the overall sensitivity of the test. p53 is a well-known tumor suppressor protein that is often mutated in cancer. Such mutations may be enough to break natural immune tolerance to the protein and thus the source of anti-p53 antibodies. NY-ESO-1 has been characterized as a tumor specific marker and thus autoantibodies against this protein may represent a way to measure the levels of a tumor marker in early stage disease via immune amplification. MAPKAPK3 is a kinase protein that can be activated by several oncogenic pathways and thus may be more commonly up-regulated in lung cancer leading to the development of autoantibodies targeted against it.

In certain embodiments, the method for determining a quantified increased risk for the presence of a lung cancer in an asymptomatic human subject, comprises: 1) measuring a panel of markers in sample from a human subject that is at least 50 years of age or older and has a history of smoking tobacco; 2) determining a normalized score for each marker; 3) summing the normalized score to obtain a composite score for the human subject, 4) quantifying the increased risk for the presence of the lung cancer for the human subject as a risk score, wherein the composite score is matched to a risk category of a grouping of stratified human subject populations wherein each risk category comprises a multiplier indicating increased likelihood of having the lung cancer correlated to a range of composite scores; and, 5) providing a risk score for the human subject, whereby the quantified increased risk for the presence of the lung cancer in an asymptomatic human subject has been determined.

In certain embodiments, the step of normalizing comprises determining the multiple of median (MoM) score for each marker. In this instance, the MoM score is the subsequently summed to obtained a composite score.

It is understood that the disease cohort (e.g. a human subject that is at least 50 years of age or older and has a history of smoking tobacco) is independently determined and in this instance is well understood to be the "at risk" group for developing lung cancer. This present method and algorithm re-categorizes those at-risk patients into risk categories quantifying their true increased risk for the presence of lung cancer over the disease cohort.

In other embodiments, provided herein are methods of assessing the likelihood that a patient has lung cancer relative to a population comprising the steps of: obtaining a sample from the patient; measuring the levels of multiple biomarkers in the sample; calculating a composite score from the biomarker measurements; comparing the patient composite score to the composite scores of persons known to be at a high and a low risk for lung cancer; and determining the level of risk of the patient for having lung cancer relative to the population.

In this instance, an asymptomatic patient's cancer risk level, relative to a population, is determined. In certain embodiments, the determination may comprise quantifying the risk level relative to a population. In other aspects, the multiple biomarkers comprise two or more, three or more, four or more, five or more or six or more biomarkers. In one embodiment, the multiple biomarkers comprise six markers selected from CEA, CA125, Cyfra 21-1, Pro-GRP, anti-NY-ESO-1, anti-p53, anti-Cyclin E2 and anti-MAPKAPK3.

In other embodiments, obtaining a composite score may further comprise normalizing the measured biomarker values and summing the normalized values to generate a composite score.

iii) Normalization of Data

In certain embodiments, the value obtained from measuring the marker in the sample is normalized. There is no intended limitation on the methodology used to normalize the values of the measured biomarkers provided that the same methodology is used for testing a human subject sample as was used to generate the Risk Categorization Table.

Many methods for data normalization exist as are familiar to those skilled in the art. These include methods as simple as background subtraction, scaling, multiple of the median (MoM) analysis, linear transformation, least squares fitting, etc. The goal of normalization is to equate the varying measurement scales for the separate markers such that the resulting values may be combined according to a separate a weighting scale as determined and designed by the user and are not influenced by the absolute or relative values of the marker found within nature.

US Publ. No. 2008/0133141 (herein incorporated by reference) teaches statistical methodology for handling and interpreting data from a multiplex assay. The amount of any one marker thus can be compared to a predetermined cutoff distinguishing positive from negative for that marker as determined from a control population study of patients with cancer and suitably matched normal controls to yield a score for each marker based on said comparison; and then combining the scores for each marker to obtain a composite score for the marker(s) in the sample.

The predetermined cutoffs can be based on ROC curves and the score for each marker can be calculated based on the specificity of the marker. Then, the total score can be compared to a predetermined total score to transform that total score to a qualitative determination of the likelihood or risk of having lung cancer.

Another method for score transformation or normalization is, for example, applying the multiple of median (MoM) method of data integration. In the MoM method, the median value of each biomarker is used to normalize all measurements of that specific biomarker, for example, as provided in Kutteh et al. (Obstet. Gynecol. 84:811-815, 1994) and Palomaki et al. (Clin. Chem. Lab. Med.) 39:1137-1145, 2001). Thus, any measured biomarker level is divided by the median value of the cancer group, resulting in a MoM value. The MoM values can be combined (namely, summed or added) for each biomarker in the panel resulting in a panel MoM value or aggregate MoM score for each sample.

In embodiments, as additional samples are tested and presence of cancer validated, the sample size of the cancer population and the normals for determining the median can be increased to yield more accurate population data.

In certain embodiments, normalization comprises determining a multiple of median (MoM) score for each biomarker measured.

In the next step of the present methods, the normalized value for each biomarker is summed to provide a composite score for each subject. In certain embodiments, this method comprises summing the MoM score to obtain a composite score.

In other words, the composite score is derived by measuring the levels of each of all markers used in a panel for a particular cancer in arbitrary units and comparing these levels to the median levels found in previous validation studies. In one embodiment, the cancer is lung cancer and the panel comprises the six markers disclosed above wherein this method generates six initial scores representing the multiple of the median (MoM) for each marker for a given patient. These initial scores are summed to yield the final composite score.

In certain embodiments, the markers are measured and those resulting values normalized and then summed to obtain a composite score. In certain aspects, normalizing the measured biomarker values comprises determining the multiple of median (MoM) score. In other aspects, the present method further comprises weighting the normalized values before summing to obtain a composite score.

D) Risk Categorization Table

The next step of the present method comprises quantifying the increased risk for the presence of the cancer for the human subject as a risk score, wherein the composite score is matched to a risk category of a grouping of stratified human subject populations wherein each risk category comprises a multiplier indicating increased likelihood of having the cancer correlated to a range of composite scores. This quantification step is based on the predetermined grouping of a stratified cohort of human subjects. In one embodiment, the grouping of a stratified population of human subjects, or stratification of a disease cohort, is in the form of a risk categorization table. The selection of the disease cohort, the cohort of human subjects that share cancer risk factors, are well understood by those skilled in the art of cancer research. In certain embodiments, the cohort may share an age category and smoking history. However, it is understood that the cohort, and the resulting stratification, may be more multidimensional and take into account further environmental or biological factors (e.g. epidemiological factors).

In certain embodiments, the grouping of a stratified human subject population used to determine a quantified increased risk for the presence of a cancer in an asymptomatic human subject, comprises: at least three risk categories, wherein each risk category comprises 1) a multiplier indicating increased likelihood of having the cancer, 2) a risk identifier and 3) a range of composite scores. In certain aspects, wherein an individual risk score is generated by summing the normalized values determined from a panel of markers for the cancer to obtain a composite that is correlated to a risk category of the risk categorization table. In a further aspect, the normalized values are determined as multiple of median (MoM) scores.

The risk identifier is a label given to a specific group to provide context for the range of risk scores and the multiplier indicating increased likelihood of having the cancer in each grouping. In certain embodiments, the risk identifier is selected from low risk, intermediate-low risk, intermediate risk, intermediate-high risk and highest risk. These risk identifiers are not intended to be limiting, but may include other labels are dictated by the data used to generate the table and/or further refine the context of the data.

The multiplier indicating increased likelihood of having the cancer is a numerical value, such as 13.4; 5.0; 2.1; 0.7; and 0.4. This value is empirically derived and will change depending on the data, cohort of the subject population, type of cancer, biomarkers, etc. and so on. Thus, the multiplier indicating increased likelihood of having the cancer is a numerical value selected from 2, 3, 4, 5, 6, 7, 8, 9, 10, 11, 12, 13, 14, 15, 16, 17, 181, 19 20, 21, 22, 23, 24, 25, 26, 27, 28, 29, and 30, and so on, or some fraction thereof. The value indicates the increased risk, over the normal prevalence of cancer in the cohort population that formed the basis for the stratification, for the human subject at the time of testing. In other words, the human subject is from the same disease cohort as the one used to generate the risk categorization table. In the example of lung cancer, a disease cohort may be a human subject aged 50 years or older with a history of smoking tobacco. Thus, for example, if a patient receives a risk score of 13.4, then that human subject has a 13.4 times increased risk for the presence of the cancer relative to the population.

As disclosed above, this multiplier value is empirically determined and in the present instance is done using retrospective clinical samples. As such the stratification of human subjects is based on analysis of retrospective clinical samples from subjects having a cancer wherein the actual incidence of cancer, or the positive predictive score, is determined for each stratified grouping. The specifics of this are detailed below and in the example section.

In general, once a population of human subjects has been stratified a positive predictive score can be determined, when retrospective samples with a known medical history are used, for each stratified grouping. This actual incidence of cancer in each of these groups is then divided by the reported incidence of cancer across the population of human subjects. For example, if the positive predictive score for one of the groupings from the stratified population of human subjects was 27%, this value would then be divided by the actual incidence of cancer across the cohort of the population that was stratified (e.g. 2%) to yield a multiplier of 13.5. In this scenario, the multiplier indicating increased likelihood of having the cancer is 13.5 and a subject tested that had a composite score matched to this category would have a risk factor of 13.5. In other words, at the time of testing, that human subject would be 13.5 times more likely to have the presence of cancer than the general population in that particular cohort.

Thus, for example, a bead immunoassay was used to screen selected patients with lung cancer and normal individuals for the presence of a panel of three autoantibody and three antigen markers associated with lung cancer in a blinded study. One hundred thirty-four lung cancer patients and 121 age-matched smokers without lung cancer as controls contributed blood samples for testing. The assay employed fluorescence reporters and the degree of fluorescence was machine reported as a mean fluorescence intensity with a value ranging from 0 (lowest) to 5 (highest). The values obtained for each marker in the lung cancer population provided a median value, which then was used to determine the MoM value for experimental samples.

The plotted ROC curve has an AUC of 0.738. The specificity was 80% and the sensitivity was 59%.

The aggregate scores from the lung cancer patients and the normal cohort stratified into five ranges. The specificity and sensitivity of each range was determined, where the sensitivity represented the number of cancer patients with scores in any one range divided by the total number of cancer patients, 134. The specificity was the number of the normal cohort with a score in that range subtracted from 121, divided by 121.

That stratification enabled a data transformation into a more qualitative risk categorization providing a greater degree of information for subsequent choices in light of the costs of lung cancer confirmation, for example a CAT scan or a PET scan, as well as patient compliance. Hence, because lung cancer incidence in the at risk population of heavy smokers is about 2%, that percentage was used as the cutoff point between likelihood of cancer and not, meaning, at that level the individual had an even chance of having cancer, that is, 1. Positive predictive values were determined using the disease prevalence of 2% and then that positive predictive value was divided by two to yield another risk value interpreted as the likelihood of having lung cancer as a multiple of that of the normal population risk, which can be considered as 1 or even chances, or as a 2% risk based on population studies.

The resulting risk categorization table is provided in FIG. 1. The third component of each risk category of the Risk Categorization Table is a range of composite scores. In the example provided above these composite scores were generated from normalizing the data from the panel of measured biomarkers and then summing the individual values from each marker per sample. These composite scores were then grouped to provide a range and drove the stratification of the population. The specifics of this methodology are detailed below in the Example section.

Transforming the composite score to a risk category that is based on population data, the physician and patient then can assess whether follow-up is required, necessary or recommended based on whether there is a greater risk that is just slightly above that of any smoker, i.e., 2%, or is higher because of a greater composite score, which may be deserving of greater consideration by the patient.

By further data transformation of the positive predictive value, the physician and patient will be the beneficiary of a quantitative value with foundation in the prevalence of cancer amongst smokers which provides improved resolution on the risk of cancer in light of the biomarker assay. Hence, a patient with a composite biomarker score of 20 or greater has a 13-fold greater likelihood of having lung cancer than any other heavy smoker, See FIG. 1. That 13.4× multiplier translates to an overall risk of about 27% of having lung cancer. That is, while all heavy smokers have a 1 in 50 chance of having lung cancer prior to testing, with a composite score or 20 or more after testing, that individual has a 1 in 4 chance of having lung cancer. Therefore, that person should consider a follow-up to visualize whether any cancer is present.

Thus, in certain embodiments, the method for determining a quantified increased risk for the presence of lung cancer in an asymptomatic human subject, comprises: 1) measuring a level of CEA, CA125, Cyfra 21-1, anti-NY-ESO-1, anti-p53 and anti-MAPKAPK3 in a serum sample from the human subject, wherein the human subject is at least 50 years of age or older and has a history of smoking tobacco; 2) determining a normalized score for each marker; 3) summing the normalized score to obtain a composite score for the human subject, 4) quantifying the increased risk for the presence of the lung cancer for the human subject as a risk score, wherein the composite score is matched to one of at least three risk categories of a grouping of a stratified human subject population wherein each risk category comprises a multiplier indicating increased likelihood of having the lung cancer correlated to a range of composite scores; and, 5) providing a risk score for the human subject, whereby the quantified increased risk for the presence of the lung cancer in an asymptomatic human subject has been determined.

In certain embodiments, the step of normalizing comprises determining the multiple of median (MoM) score for each marker. In this instance, the MoM score is then subsequently summed to obtain a composite score.

After quantifying the increased risk for presence of the cancer in the form of a risk score, this score may be provided in a form amendable to understanding by a physician. In certain embodiments the risk score is provided in a report. In certain aspects, the report may comprise one or more of the following: patient information, a Risk Categorization Table, a risk score, a test score, a composite score, identification of the risk category for the patient, an explanation of the Risk Categorization Table and the resulting test score, list of biomarkers tested, description of the disease cohort, and so on.

E) Use of Methods to Aid in the Early Detection of Lung Cancer

The use in a clinical setting of the methods and algorithms according to the present invention are now described in the context of lung cancer screening. It should be appreciated, however, that lung cancer is only one of many cancer types that can benefit from the present invention.

Primary care healthcare practitioners, who may include physicians specializing in internal medicine or family practice as well as physician assistants and nurse practitioners, are among the users of the methodology disclosed herein. These primary care providers typically see a large volume of patients each day and many of these patients are at risk for lung cancer due to smoking history, age, and other lifestyle factors. In 2012 about 18% of the U.S. population was current smokers and many more were former smokers with a lung cancer risk profile above that of never smokers.

The aforementioned NLST study (See, background section) concluded that heavy smokers over a certain age who undergo yearly screening with CT scans have a substantial reduction in lung cancer mortality as compared to those who are not similarly screened. Nevertheless, for the reasons discussed above, very few at risk patients are undergoing annual CT screening. For these patients the testing paradigm according to the present invention offers an alternative.

A blood sample from patients with a heavy smoking history (e.g. having smoked at least a pack of cigarettes per day for 20 years or more) is sent to a laboratory qualified to test the sample using a panel of biomarkers with adequate sensitivity and specific for early stage lung cancer. Non limiting lists of such biomarkers are herein included in the above disclosure and the following examples. In lieu of blood, other suitable bodily fluids such a sputum or saliva might also be utilized.

A biomarker composite score for that patient is then generated using the technique described in the present disclosure. Using the composite score the patient's risk of having lung cancer, as compared to others having a comparable smoking history and age range, can then be calculated using a table such as the one show in FIG. 1. In lieu of the tabular format shown other means of calculation may be employed including those which utilize a computer program. In particular, if the risk calculation is to be made at the point of care, rather than at the laboratory, a software application compatible with mobile devices (e.g. a tablet or smart phone) may be employed in lieu of a table.

Once the physician or healthcare practitioner has a risk score for the patient (i.e. the likelihood that that patient has lung cancer relative to a population of others with comparable epidemiological factors) they can recommend, in particular, that those at a higher risk be followed up with other tests such as CT scanning. It should be appreciated that the precise numerical cut off above which further testing is recommended may vary depending on many factors including, without limitation, (i) the desires of the patients and their overall health and family history, (ii) practice guidelines established by medical boards or recommended by scientific organizations, (iii) the physician's own practice preferences, and (iv) the nature of the biomarker test including its overall accuracy and strength of validation data.

It is believed that use of the methodology disclosed herein will have the twin benefits of ensuring that the most at risk patients undergo CT scanning so as to detect early tumors that can be cured with surgery while reducing the expense and burden of false positives associated with stand-alone CT screening.

F) Kits

One or more biomarkers, one or more reagents for testing the biomarkers, cancer risk factor parameters, a Risk Categorization Table, algorithm for calculating a risk score, and any combinations thereof are amenable to the formation of kits (such as panels) for use in performing the present methods.

In certain embodiments, the kit can comprise (a) reagents containing at least one antibody for quantifying one or more antigens in a test sample, wherein said antigens comprise one or more of: cytokeratin 8, cytokeratin 19, cytokeratin 18, CEA, CA125, CA15-3, SCC, CA19-9, proGRP, Cyfra 21-1, serum amyloid A, alpha-1-anti-trypsin and apolipoprotein CIII; (b) reagents containing one or more antigens for quantifying at least one antibody in a test sample; wherein said antibodies comprise one or more of: anti-p53, anti-TMP21, anti-NPC1L1C-domain, anti-TMOD1, anti-CAMK1, anti-RGS1, anti-PACSIN1, anti-RCV1, anti-MAPKAPK3, anti-NY-ESO-1 and anti-Cyclin E2; and (c) one or more algorithms or computer programs for performing the steps of normalizing the amount of each antigen and/or antibody measured in the test sample, summing those normalized values to obtain a composite score and assigning a risk score or test score to each patient by correlating the composite score to a Risk Categorization Table and using the quantified increased risk for the presence of the cancer as an aid for further definitive cancer screening.

Alternatively, in lieu of one or more algorithms or computer programs, one or more instructions for manually performing the above steps by a human can be provided. The reagents included in the kit for quantifying one or more regions of interest may include an adsorbent which binds and retains at least one region of interest contained in a panel, solid supports (such as beads) to be used in connection with said absorbents, one or more detectable labels, etc. The adsorbent can be any of many adsorbents used in analytical chemistry and immunochemistry, including metal chelates, cationic groups, anionic groups, hydrophobic groups, antigens and antibodies.

In certain embodiments, the kit comprises the necessary reagents to quantify at least one of the following antigens, cytokeratin 19, cytokeratin 18, CA 19-9, CEA, CA-15-3, CA125, SCC, Cyfra 21-1, serum amyloid A, and ProGRP. In another embodiment, the kit comprises the necessary reagents to quantify at least one of the following antibodies anti-p53, anti-TMP21, anti-NPC1L1C-domain, anti-TMOD1, anti-CAMK1, anti-RGS1, anti-PACSIN1, anti-RCV1, anti-MAPKAPK3, anti-NY-ESO-1 and anti-Cyclin E2.

In some embodiments, the kit further comprises one or more algorithms or computer programs for performing some or all the steps of the method described herein. The kit may further comprise an apparatus configured with a computer program to receive the values from the evaluation of markers in a sample and making the required calculations to determine a composite score and compare it to a grouping of stratified population comprising multiple risk categories (e.g. a Risk Categorization Table) and provide a Risk Score.

G) Apparatus

The present invention further provides for an apparatus for assessing a subject's risk level for the presence of cancer and correlating with an increase or decrease of the presence of cancer after testing relative to a population. The apparatus comprises a computer program or software application to receive the values from the evaluation of markers in a sample and make the required calculations to determine a composite score and compare it to a grouping of stratified population comprising multiple risk categories (e.g. a Risk Categorization Table) and provide a Risk Score. The methods for obtaining and calculating a composite score and risk score are described above.

The apparatus can take one of a variety of forms, for example, the correlation and means of matching can be provided as a computer program in any format known to a person of ordinary skill in the art that allows the method to be implemented in a handheld device, a tablet, or any other type of computer or electronic device, the apparatus can be a computer software product, an application for a handheld device, a handheld device configured to performed the method, or it can be a world-wide-web (WWW) page or other network accessible location, or it can be a computing device. Alternatively, the apparatus can be a simple functional representation of the correlation such as a nomogram provided on a card, or wheel, that is readily portable and simple to use. For example, the apparatus can be in the form of a laminated card or wheel. Accordingly, the correlation can be a graphic representation, which, in some embodiments, is stored in a database or memory, such as a random access memory, read-only memory, disk, virtual memory or processor. Other suitable representations, pictures, depictions or exemplifications known in the art may also be used.

The apparatus may further comprise a storage means for storing the correlation or nomogram, an input means that allows the input into the apparatus of the identical set of factors determined for a subject, and a display means for displaying the status of the subject in terms of the particular medical condition. The storage means can be, for example, random access memory, read-only memory, a disk, virtual memory, a database, or a processor. The input means can be, for example, a keypad, a keyboard, stored data, a touch screen, a voice-activated system, a downloadable program, downloadable data, a digital interface, a hand-held device, or an infrared signal device. The display means can be, for example, a computer monitor, a cathode ray tube (CRT), a digital screen, a light-emitting diode (LED), a liquid crystal display (LCD), an X-ray, a compressed digitized image, a video image, or a hand-held device. The apparatus can further comprise a database, wherein the database stores the correlation of factors and is accessible to the user.

In one embodiment of the present invention, the apparatus is a computing device, for example, in the form of a computer or hand-held device that includes a processing unit, memory, and storage. The computing device can include, or have access to a computing environment that comprises a variety of computer-readable media, such as volatile memory and non-volatile memory, removable storage and/or non-removable storage. Computer storage includes, for example, RAM, ROM, EPROM & EEPROM, flash memory or other memory technologies, CD ROM, Digital Versatile Disks (DVD) or other optical disk storage, magnetic cassettes, magnetic tape, magnetic disk storage or other magnetic storage devices, or other medium known in the art to be capable of storing computer-readable instructions. The computing device can also include or have access to a computing environment that comprises input, output, and/or a communication connection. The input can be one or several devices, such as a keyboard, mouse, touch screen, or stylus. The output can also be one or several devices, such as a video display, a printer, an audio output device, a touch stimulation output device, or a screen reading output device. If desired, the computing device can be configured to operate in a networked environment using a communication connection to connect to one or more remote computers. The communication connection can be, for example, a Local Area Network (LAN), a Wide Area Network (WAN) or other networks and can operate over a wired network, wireless radio frequency network, and/or an infrared network.

All references cited herein are herein incorporated by reference in entirety.

EXAMPLES

The Examples below are given so as to illustrate the practice of this invention. They are not intended to limit or define the entire scope of this invention.

Example 1

Study of Lung Cancer Biomarker Expression in Retrospective Clinical Samples

Over 1000 blood samples from patients with all stages of lung cancer, the at risk population (20 pack-year smokers over 50 years of age) and various other control groups including those with non-cancerous lung disorders and other cancers (prostate, breast and colorectal) are provided herein (See, FIG. 2). These samples were collected from multiple cohorts of patients over a 5 year period from several sites both in the United States and in Europe.

FIG. 3 shows a receiver operator characteristic (ROC) curve analysis of all lung cancer vs. all non-cancer samples yielded an area under the curve (AUC) of 0.76. Choosing a cutoff of 10.7 shows a specificity of 80% yields a sensitivity of 64%. The data was further analyzed as a function of tumor stage using the same cutoff and yielding 75% sensitivity in late stage disease and 59% sensitivity for early stage disease indicating that the test has a higher sensitivity for later stage disease. Amongst the non-cancerous patients, the specificity of the test was not affected by either smoking status or the presence of noncancerous lung disorders (including asthma, COPD, emphysema, fibrosis and pneumonia) all of which yielded scores in the same proportions as the overall normal population. Analysis of the scores of three other cancer types (prostate, breast and colorectal) demonstrated that these other cancers can yield a higher score more often than non-cancerous conditions, but that the range and median of scores is more similar to that found in the normal population.

A further validation study was performed using a cohort of 322 samples obtained with the specific intent of early detection of cancer in the high risk population (FIG. 4). All of the cancers in this study were early stage cancers and the control group specifically consisted of age-matched long-term heavy smokers. An ROC curve analysis was again performed and yielded an AUC of 0.73 (FIG. 5). Applying the cutoff determined in the development stage yielded a specificity of 80% and a sensitivity of 57%.

Example 2

Validation of Biomarker Panel and Assay Redesign

Applicants redesigned the assay system to allow for multiplexing of biomarker detection and thus increased efficiency in the clinical diagnostic lab. As part of this work, Applicants performed a full analytical validation of the test in accordance with standard clinical laboratory practice. Specifically, assay linearity, precision and reproducibility were assessed for each of the six biomarkers. FIG. 6 presents the linearity of one of the tumor markers in a spike and recovery assay. All 6 biomarkers, those disclosed above, are detected in the linear range and have $r^2$ values of >0.9. Precision and repeatability were determined by testing 3 samples twice a day for 5 days each for two independent operators. An additional 5 days of data were collected for a single operator. All testing was performed in duplicate. FIG. 7 displays representative data for 3 of the markers.

A clinical bridging study was also performed in which 181 blood samples that had been previously tested by others were retested using the redesigned assay. The data indicated a slight decrease in the clinical specificity and sensitivity of the assay in the redesigned system. This loss was deemed acceptable as it may be attributable to some loss in sample integrity due to the aging and handling of the tested samples in the period of time since the original testing by others.

Example 3

Final Validation Study

The Applicants a blinded retrospective study of the present methods using a total of 255 patients including 134 confirmed diagnoses of lung cancer and 121 age-matched >20 pack-year smokers as controls. The study group included two cohorts of patients collected at two separate cancer centers; one in the Northeastern United States and one in the Southwest. Cancer patients were a mix (~50:50) of early and late stage. All six biomarkers were tested and analyzed to yield the composite score. The data is presented as a box plot in FIG. 8. A ROC curve analysis yielded an AUC of 0.74 and applying a cutoff to hold the specificity at 80% yields a sensitivity of 59% FIGS. 4B & C). This data is in good agreement with the previous studies (FIGS. 2-5).

Example 4

Clinical Utility and Risk Categorization

The above described biomarker panel and methods are intended for use as an aid to determine which high-risk patients need to be directed to appropriate non-invasive diagnostic follow-up, especially chest CT scan for patients at high-risk for lung cancer. More specifically, it is intended for asymptomatic individuals ≥50 years of age with a history of tobacco use of ≥20 pack-years and who are either current or former smokers. This test is not indicated for individuals who have had a previous diagnosis of cancer, or who currently have symptoms indicative of lung cancer, or who are already enrolled in and complying with an annual CT screening program. The test is not for use to render a diagnosis of lung cancer; a definitive diagnosis of lung cancer can only be rendered histologically and/or cytologically.

The test generates a risk score based on the levels of 6 biomarkers in patient serum. This score is an indicator of the level of risk for each patient of currently having lung cancer relative to others with a comparable smoking history. Applicants have herein developed a risk categorization tool based on test experience resulting from retrospective studies performed during the development of the test (FIG. 1). This table indicates the likelihood that a patient in a given score range has cancer at the time of testing. Likelihoods are based on a known prevalence of lung cancer of 1.5-2.0% in the at-risk population (>50 years of age, >20 pack-years smoking history). The result of the test informs the physician to determine whether the risk that a patient has cancer warrants that he/she should be followed up with chest CT scan. The decision for follow up is also based on specific factors associated with the individual patient (overall health, family history, insurance, interest level in early detection, etc.)

An expanded table (FIG. 9) indicates the sensitivity, specificity, accuracy, positive and negative predictive values obtained from the present methods when all patients with a score above the given value are proscribed for further follow-up. The table further indicates the number of cancers detected and the number of false positive results generated out of a patient base of 1000 high-risk individuals when the given cutoff is used. Note, for example, that if all individuals with an Intermediate Risk or higher are sent to CT, 10 out of 20 cancers (50%) will be detected early while only 137 out of 1000 (14%) of asymptomatic, heavy smokers over age 50 will need to be subjected to CT scanning. Using this cutoff would substantially reduce false positives associated with CT screening but could miss as many as half of early cancers if the blood test is given only once. (We anticipate fewer false negatives from serial testing 1-2 times per year.) It should be noted that even with a sensitivity of 51%, a patient with a score below 9 only has about a 1% chance of having lung cancer at the time of the test based on our data. On the other hand, referring all patients with at least an Intermediate-Low Risk (i.e. test score of greater than 6) would improve sensitivity to better than 80% but would make less of an improvement in reducing the false positive rates of CT scans.

The present risk categorization table and method for lung cancer is a multiplex immunoassay that determines the risk of the presence of lung cancer in asymptomatic individuals who are greater than 50 years of age and current or former smokers with greater than or equal to a twenty pack-year smoking history (less than or equal to 15 years since last use of tobacco for former smokers). The test analyzes six biomarkers that give a composite score that categorizes patients into lung cancer risk categories based on empiric data from retrospective clinical studies. It is intended that results of this test are to be used in conjunction with other clinical data to determine the appropriate diagnostic follow up.

Example 5

Validation of the Algorithm to Determine in Asymptomatic Human Subjects a Quantified Increased Risk for the Presence of Lung Cancer A multiplex diagnostic platform is an automated comprehensive system capable of isolating the target analyte (protein antigen or autoantibody), performing the test, and displaying the interpretation of the multiplex test result. To accomplish our multiplexed test we use a flow cytometry bead-based approach. Multiplex bead array assays provide quantitative measurement of large numbers of analytes using an automated 96-well plate format. The Luminex method uses microsphere sets carrying variable quantities of two different fluorescent dyes that produce up to 100 different shades of color. Each bead is coupled to a unique antibody or protein that recognizes a specific molecule. After the beads are mixed with a serum sample and added to the instrument, the unique color signature on each bead reveals the identity of the bound molecules. The level of fluorescence (reported as Median Fluorescence Intensity or MFI) of the tagged antibody or protein indicates the level of antibody or protein in the serum.

Our panel of biomarkers includes 3 autoantibodies (p53 (Pierce RP-39232), NY-ESO-1(Pierce RP-39227), and Mapkapk3 (Genway 10-782-55070)) and 3 tumor markers (CA125, CEA and CYFRA 21-1). These three autoantibody markers as well as the protein CEA marker (anti-CEA, Abcam ab4451) are produced in-house using the Luminex beads/plateform technology. Commercially available reagents for CA125 and Cyfra 21-1 (Millipore HCCBP1MAG-58K-02) are used.

Autoantibody Assay

In this assay, protein (antigen) is coupled to Luminex beads. The beads (with 3 unique color signatures each with a single biomarker protein) are then incubated with the patient serum (capture of the specific autoantibody). After incubation and washing steps the bead/antibody complex is exposed to the fluorescent labeled anti-human reporter antibody (Thermo, PAI-86078). The complex is then washed again and then placed in the Luminex instrument. The color signature distinguishes the biomarker being measured and the median fluorescence intensity of the reporter indicates the amount of the autoantibody of interest. NY-ESO-1 is coupled to Luminex bead, region 35 (Luminex, MC10035), p53 is coupled to Luminex bead, region 43 (Luminex, MC10043) and MapkapK3 is coupled to Luminex bead, region 45 (Luminex, MC10043)

Tumor Protein Assay

In this assay an antibody to the protein of interest is coupled to a surface-Luminex bead. The bead is then incubated with the patient serum. The protein of interest binds to the antibody coated bead (capture). Next, a second antibody (detection) is incubated with the capture antibody-protein complex. The detection antibody is labeled with a fluorescent tag. After washing unbound material away, the complex or "sandwich" (capture antibody-protein-detection antibody) is placed in the Luminex instrument. The color signature of the Luminex bead indicates the analyte being measured and the Median Fluorescent Intensity (MFI) measures the amount of protein biomarker present in the sample.

The two assays have different incubation times etc, so for this reason two separate multiplex assays are performed. The data is combined and the output placed into our data analysis sheet/calculator. The values from each of the markers is normalized by calculating the multiple of median (MoM) score for each individual marker and then the sum of all six MoM scores are correlated to a risk category of the Risk Categorization Table. This risk score is provided in a report to the physician for their use.

For example, the mean Fluorescent Intensity (data not shown) of each marker tested from patient samples, as determined by the MagPix Instrument, were transferred to a Data Analysis Worksheet. The mean, standard deviation and % CV were then calculated for the triplicate MFI values. After background, MFI was subtracted and the MoM was calculated for each marker. After the individual medians of the six markers were calculated, they are added together to provide an aggregate or composite score. The sum of the MoM values (or composite score) was then assigned to the patient and reported as the increased risk for the presence of lung cancer. The numerical value for the risk score was obtained by correlating the composite score to the Risk Categorization Table.

Example 6

Generation of a Risk Categorization Table for Lung Cancer

The stepwise construction of a risk categorization table was performed as follows. See, FIG. 1. First, a table of data was constructed by performing the multi-analyte test on a cohort comprising 121 control non-cancer subjects and 134 lung cancer subjects. For each subject of the study, in one row of a spreadsheet program (Microsoft EXCEL) the sum of the MOMs for the six markers was aligned with the clinical condition, i.e. cancer or non-cancer, such that all subjects of the same condition were in contiguous rows. (To facilitate performance of the following steps manually, at this point the data may be sorted by scores in descending or ascending order before proceeding.) The second step was to select a specific number of risk categories that are considered to be clinically relevant to the relative need to perform follow-up procedures. In this example it was decided to use five risk categories. Thirdly, each of five risk categories was assigned a range of MOM scores, in which increasing MOM score ranges would be associated with higher risk categorizations. Five ranges were defined by selecting the 5 pairs of specific cutoffs, which were: ">20" (highest risk); $14<score\leq20$ (Intermediate-High Risk); $9<score\leq14$ (Intermediate Risk); $6<score\leq9$ (Intermediate-Low Risk); and $score\leq6$ (Low Risk). In statistics and diagnostic testing, the positive predictive value, or precision rate is the proportion of positive test results that are true positives (such as correct diagnoses). For each risk category, a positive predictive value was calculated by using a standard formula known in the art, which is applicable to data from cohort studies in which arbitrary numbers of disease and control subjects are selected by the experimenter, which is:

PPV=SE*PR/((SE*PR)+(1−SP)*(1−PR))

In which PPV is the Positive Predictive value;
SP is the specificity which is defined by the formula (negative tests, disease absent)/[(negative tests, disease absent)+(positive tests, disease absent)];
SE is the sensitivity which is defined by the formula (positive tests, disease present)/[(positive tests, disease present)+(negative tests, disease present)];
and the prevalence (PR) is an estimate of the frequency of occurrence of the disease in the population of individuals who are to be screened for the disease, as restricted by known risk factors for the disease (i.e. for lung cancer, the known major epidemiological risk factors include age, gender, smoking intensity, and possibly time since cessation of tobacco use). See, FIGS. 9 and 10. [Bach, P. B., et al., Variations in Lung Cancer Risk Among Smokers. Journal of the National Cancer Institute, 2003. 95(6): p. 470-478.; Bach, P. B., et al., Screening for Lung Cancer*ACCP Evidence-Based Clinical Practice Guidelines (2nd Edition). CHEST Journal, 2007. 132(3_suppl): p. 69S-77S.; Spitz, M. R., et al., A Risk Model for Prediction of Lung Cancer. Journal of the National Cancer Institute, 2007. 99(9): p. 715-726.; Tammemagi, C. M., et al., Lung Cancer Risk Prediction: Prostate, Lung, Colorectal and Ovarian Cancer Screening Trial Models and Validation. Journal of the National Cancer Institute, 2011. 103(13): p. 1058-1068.] Furthermore for each risk category, to calculate the post-test risk of having cancer given a positive blood test, the positive predictive value was then divided by the prevalence of lung cancer or pretest epidemiologic risk of having lung cancer as obtained from epidemiological studies. In those calculations, the final calculation is a dimensionless number because it is a ratio of two decimal fractions i.e. positive predictive value divided by the subject's lung cancer prevalence given an age range and a range of behavioral smoking intensity such as may be mitigated by recent smoking cessation. This number is the subject's absolute, post-test, fold risk of having lung cancer, as compounded of both their estimated personal risk factors and the result of their blood test result.

It is also possible to elaborate a further series of more accurate risk stratification tables that could be devised to tailor the predicted post-test risk to account for the dependence of the subject's pre-test risk on various factors which include age, gender, smoking intensity and years since smoking cessation. It is further possible to employ a recursive strategy to devise risk categories that result in a pre-determined series of risk levels, such a 0.5-fold, 1.0-fold, 3-fold, 5-fold and 10-fold, which could be derived by modifying the cutoffs until the required categories of a series are realized.

Example 7

Patient Test Results

In the latter half of 2012 a blood test for the early detection of lung cancer was offered to primary care physicians in the Washington, D.C. area. Approximately 250 blood samples were received, tested and scored according to the method of the present invention. See the website, BloodTestforLungCancer. The test results, including the risk score, were reported to the treating physician. The Aggregate MoM Values for these patients ranged from 0 to 248 with 5% deemed to equate to an intermediate risk or higher (see Risk Categorization Table, FIG. 1).

For most of these samples, approximately 2 ml of blood were drawn in a serum separator tube then spun, sent to the laboratory, and within two days the multiplex biomarker test was performed in the manner set forth in the preceding Examples. Six proteins were analyzed in the panel on the Luminex Magpix including 3 cancer biomarkers and 3 autoantibodies. For the cancer biomarkers, five microliters of plasma were diluted in 95 microliters of buffer and for the autoantibodies, three microliters of plasma are diluted in 57 microliters of buffer. These were run in triplicate and the negative control values were subtracted from these values. Median of the mean (MOM) was calculated for each of the proteins by dividing these average-background values for the patient by the median value for all patients. The score was determined by the sum of the MOM values.

In December 2012 a blood sample from a 51 year old high-risk patient was received and tested according to the methodology set forth in the preceding Examples. The Aggregate MoM Value (i.e. Composite Score) for this patient was determined to be score reported as 120 corresponding to the highest risk for lung cancer (at least 13.4 times increased likelihood of having lung cancer in the high-risk smoking population).

TABLE A

Data and result of lung cancer test for the patient with Composite Score of 120.

| | Cancer Biomarkers | | | Autoantibodies | | |
|---|---|---|---|---|---|---|
| | CEA | CA125 | Cyfra | NY-ESO-1 | p53 | MAPKAK3 |
| Average Value | 1927.5 | 106.8 | 73.5 | 14.5 | 16.5 | 14.2 |
| Average Background | 17.0 | 17.3 | 34.0 | 20.0 | 7.3 | 12.7 |
| Average value-Background (Av-Bkg) | 1910.5 | 89.4 | 39.5 | −5.5 | 9.2 | 1.5 |
| Median | 19 | 10 | 4 | 33 | 83 | 41 |
| MOM (Av-Bkg/Median) | 100.6 | 8.9 | 9.9 | −0.1 | 0.1 | 0.0 |
| SUM | 119.4 | | | | | |

A chest CT scan was performed 4 days later that showed a 5.4 cm mass at the hilum of the right lung and a PET scan performed the same day was positive consistent with the presence of lung cancer. Patient has been referred to an oncologist for further evaluation.

The results from these 250 patient samples demonstrates in a real world clinical setting that the method and algorithm according to the present invention assists in categorizing some patients as lower risks and others as higher risk.

What is claimed is:
1. A method comprising:
   a) obtaining a sample from a human subject asymptomatic for lung cancer;
   b) measuring a panel of markers in the sample, wherein at least two of the markers are selected from CEA, CA125, Cyfra 21-1, Pro-GRP, anti-NY-ESO-1, anti-p53, anti-Cyclin E2 and anti-MAPKAPK3;
   c) determining a multiple of median (MoM) score for each marker;

d) summing the MoM score to obtain a composite score for each human subject, quantifying the increased risk for the presence of lung cancer for the human subject as a risk score, wherein the composite score is matched to a risk category of a grouping of stratified human subject populations wherein each risk category comprises a multiplier indicating increased likelihood of having the lung cancer correlated to a range of composite scores as compared to use of a single threshold value, wherein the multiplier is determined from positive predictive scores of retrospective samples; and, e) administering a computerized tomography (CT) scan to the human subject with a quantified increased risk for the presence lung cancer.

2. The method of claim 1, wherein the markers are selected from CEA, CA125, Cyfra 21-1, anti-NY-ESO-1, anti-p53 and anti-MAPKAPK3.

3. The method of claim 1, wherein the sample is blood, blood serum, blood plasma, or some part thereof.

4. The method of claim 1, wherein the grouping of a stratified human subject population, the multiplier indicating increased likelihood of having the cancer and the range of composite scores are determined from retrospective clinical samples of a population.

5. The method of claim 1, wherein the risk category further comprises a risk identifier.

6. The method of claim 5, wherein the risk identifier is selected from low risk, intermediate-low risk, intermediate risk, intermediate-high risk and highest risk.

7. The method of claim 1, wherein calculating the multiplier indicating increased likelihood of having the cancer for each risk category comprises stratifying the human cohort based on retrospective MoM scores and weighting a known prevalence of the cancer in the cohort by a positive predictive score for each stratified population.

8. The method of claim 1, wherein the grouping of a stratified human subject population comprises at least three risk categories wherein the multiplier indicating increased likelihood of having cancer is about 2 or greater.

9. The method of claim 1, wherein the grouping of a stratified human subject population comprises at least two risk categories wherein the multiplier indicating increased likelihood of having cancer is about 5 or greater.

10. The method of claim 1, wherein the human subject is aged 50 years or older and has a history of smoking tobacco.

11. The method of claim 1, further comprising generating a risk categorization table, wherein the panel of markers is measured, a multiple of median (MoM) score for each marker is determined, a composite score is obtained by summing the MoM score; determining a threshold value used to divide the composite scores into risk groups and assigning a multiplier to each group indicating the likelihood of an asymptomatic human subject having a quantified increased risk for the presence of cancer.

12. The method of claim 11, wherein the groups are in a form selected from an electronic table form, a software application, a computer program, and an excel spreadsheet.

13. The method of claim 1, wherein the panel of markers comprise proteins or polypeptides measured in a binding assay.

14. The method of claim 1, wherein the panel of markers comprise proteins or polypeptides measured using a flow cytometer.

15. A method comprising:
a) obtaining a sample from a human subject asymptomatic for lung cancer, wherein the human subject is at least 50 years of age or older and has a history of smoking tobacco;

b) measuring at least two cancer marker in the sample wherein the at least two cancer markers are selected from CEA, CA125, Cyfra 21-1, Pro-GRP, anti-NY-ESO-1, anti-p53, anti-Cyclin E2 and anti-MAPKAPK3;

c) determining a multiple of median (MoM) score for each marker measured in the sample;

d) summing the MoM score to obtain a composite score for each human subject, quantifying the increased risk for the presence of lung cancer for the human subject as a risk score, wherein the composite score is matched to one of at least three risk categories of a grouping of stratified human subject populations wherein each risk category comprises a multiplier indicating increased likelihood of having the lung cancer correlated to a range of composite scores as compared to use of a single threshold value, wherein the multiplier is determined from positive predictive scores of retrospective samples; and, e) administering a computerized tomography (CT) scan to the human subject with a quantified increased risk for the presence lung cancer.

16. The method of claim 15, wherein the panel of markers is selected from CEA, CA125, Cyfra 21-1, anti-NY-ESO-1, anti-p53 and anti-MAPKAPK3.

17. The method of claim 15, wherein the sample is blood, blood serum, blood plasma, or a component thereof.

18. The method of claim 15, wherein the composite score of the human subject is compared to the composite score of human subjects in at least three risk categories comprising those at high, intermediate, and low risk.

19. The method of claim 15, wherein the composite score of the human subject is compared to the composite score of human subjects in at least five categories comprising those at highest, intermediate high risk, intermediate risk, intermediate low risk, and low risk.

20. The method of claim 15, wherein the risk score is provided to a physician as the human subject's increased risk of having the presence of the cancer relative to a population before testing.

21. The method of claim 15, wherein calculating the multiplier indicating increased likelihood of having the cancer for each risk category comprises stratifying the human cohort based on retrospective MoM scores and weighting a known prevalence of the cancer in the cohort by a positive predictive score for each stratified population.

22. The method of claim 15, wherein the history of smoking tobacco comprises smoking at least one pack of cigarettes per day for 20 years.

* * * * *